US008728472B2

(12) United States Patent
Bibb et al.

(10) Patent No.: US 8,728,472 B2
(45) Date of Patent: May 20, 2014

(54) ANTIBODIES THAT BIND SELECTIVELY TO P25 AND USES THEREFOR

(75) Inventors: James A. Bibb, Dallas, TX (US); Janice W. Kansy, Coronado, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/375,721

(22) PCT Filed: Jun. 3, 2010

(86) PCT No.: PCT/US2010/037243
§ 371 (c)(1),
(2), (4) Date: Feb. 13, 2012

(87) PCT Pub. No.: WO2010/141710
PCT Pub. Date: Dec. 9, 2010

(65) Prior Publication Data
US 2012/0141490 A1  Jun. 7, 2012

Related U.S. Application Data

(60) Provisional application No. 61/183,694, filed on Jun. 3, 2009.

(51) Int. Cl.
*C07K 16/40* (2006.01)
*G01N 33/567* (2006.01)

(52) U.S. Cl.
USPC ................ 424/139.1; 424/146.1; 530/387.3; 530/387.9

(58) Field of Classification Search
None
See application file for complete search history.

(56) References Cited

U.S. PATENT DOCUMENTS

| 7,807,381 B2 * | 10/2010 | Bibb et al. | 435/7.1 |
| 2005/0014821 A1 | 1/2005 | Tsai et al. | 514/473 |
| 2008/0293073 A1 | 11/2008 | Bibb et al. | 435/7.1 |

FOREIGN PATENT DOCUMENTS

| WO | WO 00/21550 | 4/2000 |
| WO | WO 2004/078925 | 9/2004 |
| WO | WO 2006/075808 | 7/2006 |

OTHER PUBLICATIONS

Alvira et al., "Inhibition of the cdk5/p25 fragment formation may explain the antiapoptotic effects of melatonin in an experimental model of Parkinson's disease," *J. Pineal Res.*, 40:251-258, 2006.
Angelo et al., "Cyclin-dependent kinase 5 in synaptic plasticity, learning and memory," *J. Neurochem.*, 99:353-70, 2006.
Bibb et al., "Effects of chronic exposure to cocaine are regulated by the neuronal protein Cdk5," *Nature*, 410:376-80, 2001.
Bibb et al., "Phosphorylation of DARPP-32 by Cdk5 modulates dopamine signalling in neurons," *Nature*, 402:669-71, 1999.
Bibb et al., "Phosphorylation of protein phosphatase inhibitor-1 by Cdk5," *J. Biol.Chem.*, 276:14490-14497, 2001.
Bibb, "Role of Cdk5 in neuronal signaling, plasticity, and drug abuse," *Neurosignals*, 12:191-199, 2003.
Cheung et al., "Synaptic roles of Cdk5: implications in higher cognitive functions and neurodegenerative diseases," *Neuron*, 50:13-18, 2006.
Cruz and Tsai, "A Jekyll and Hyde kinase: roles for Cdk5 in brain development and disease," *Curr. Opin. Neurobiol.*, 14:390-394, 2004.
Cruz et al., "Aberrant Cdk5 activation by p25 triggers pathological events leading to neurodegeneration and neurofibrillary tangles," *Neuron*, 40:471-83, 2003.
Cruz et al., "p25/cyclin-dependent kinase 5 induces production and intraneuronal accumulation of amyloid β in vivo," *The Journal of Neuroscience*, 26(41):10536-10541, 2006.
Fischer et al., "Opposing roles of transient and prolonged expression of p25 in synaptic plasticity and hippocampus-dependent memory," *Neuron*, 48:825-38, 2005.
Guo, "Cyclin-dependent kinase 5—a neuronal killer?," *Sci. Aging Knowledge Environ.*, 50:36, 2003.
Hamdane et al., "Mitotic-like Tau phosphorylation by p25-Cdk5 kinase complex," *The Journal of Biological Chemistry*, 278(36):34026-34034, 2003.
Hamdane et al., "p25/Cdk5-mediated retinoblastoma phosphorylation is an early event in neuronal cell dealth," *Journal of Cell Science*, 118:1291-1298, 2005.
Hawasli et al., "Cyclin-dependent kinase 5 governs learning and synaptic plasticity via control of NMDAR degradation," *Nature Neurosci.*, 10:880-6, 2007.
Hisanaga and Asada, "Cdk5-induced neuronal cell death: The activation of the conventional Rb-E2F G1 pathway in post-mitotic neurons," *Cell Cycle*, 11(11):2049-2054, 2012.
Kusakawa et al., "Calpain-dependent proteolytic cleavage of the p35 cyclin-dependent kinase 5 activator to p25," *J. Biol. Chem.*, 275:17116-172, 2000.
Lee et al., "Neurotoxicity induces cleavage of p35 to p25 by calpain," *Nature*, 405:360-364, 2000.
Lin et al., "Involvement of Cdk5/p25 in digoxin-triggered prostate cancer cell apoptosis," *The Journal of Biological Chemistry*, 279(28):29302-29307, 2004.
Liu et al., "Comparing calpain- and caspase-3-mediated degradation patterns in traumatic brain injury by differential proteome analysis," *Biochem. J.*, 394:715-25, 2006.
Lynch et al., "LTP consolidation: substrates, explanatory power, and functional significance," *Neuropharmacol.*, 52:12-23, 2007.

(Continued)

*Primary Examiner* — John Ulm
(74) *Attorney, Agent, or Firm* — Parker Highlander PLLC

(57) ABSTRACT

The present invention relates to a monoclonal antibody or fragment thereof, which binds specifically to the cyclin-dependent kinase 5 (Cdk5) activating protein, p25 and not to p35, a hybridoma cell line producing the monoclonal antibody, and methods for the detection and/or isolation of p25, p25 fragments or homologs thereof from biological material. The invention further relates to the use of the monoclonal antibody or fragment thereof for detection and treatment of neuronal disorders and cancers.

6 Claims, 17 Drawing Sheets

(56) References Cited

OTHER PUBLICATIONS

Nath et al., "Processing of cdk5 activator p35 to its truncated form (p25) by Calpain in acutely injured neuronal cells," *Biochemical and Biophysical Research Communications*, 274:16-21, 2000.

Nguyen and Bibb, "Cdk5 and the mystery of synaptic vesicle endocytosis," *J. Cell. Biol.*, 163:697-99, 2003.

Nguyen et al., "Differential regulation of the Cdk5-dependent phosphorylation sites of inhibitor-1 and DARPP-32 by depolarization," *J. Neurochem.*, 103:1582-1593, 2007.

Nguyen et al., "Regulation of protein phosphatase inhibitor-1 by cyclin-dependent Kinase 5," *J. Biol. Chem.*, 282:16511-16520, 2007.

PCT International Preliminary Report on Patentability issued in International Application No. PCT/US2010/037243, mailed Dec. 15, 2011.

PCT International Search Report issued in International Application No. PCT/US2010/037243, mailed Nov. 30, 2010.

Sahin and Bibb, "Protein kinases talk to lipid phosphatases at the synapse," *Proc. Nat'l Acad. Sci. USA*, 101:112-113, 2004.

Sato et al., "Calpastatin, an endogenous calpain-inhibitor protein, regulates the cleavage of the Cdk5 activator p35 to p25," *J Neurochem.*, 117(3):504-515, 2011.

Wang et al., "Persistent systemic production of human factor IX in mice by skeletal myoblast-mediated gene transfer: feasibility of repeat application to obtain therapeutic levels," *Blood*, 90(3):1075-1082, 1997.

\* cited by examiner

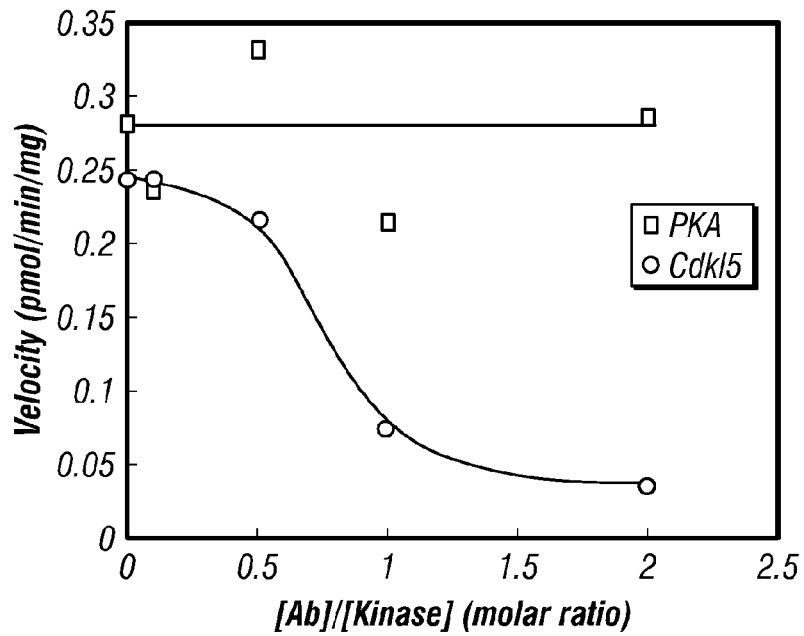

FIG. 4

Heavy Chain:
CAGATCCAGTTGGAGGAGTCTGGACCTGAGTTGAGGAAGCCTGGAGAGACA
GTCAGGATCTCCTGCAAGGCCTCTGGGTATACCTTCACAACTGCTGGAATG
CAGTGGGTGCAAAAGATGCCAGGAACGGGTCTGAAGTGGATTGGCTGGATA
AACACCCACTCTGGAGTGCCGAAATATGCAGGAGAGTTCACGGGACGGTTT
GACTTCTCTTTGGAGACCTCTGCCAGTACGGCATATTTACAGATAGTCAAC
CTCAAAAATGAGGACACGGCTACGTATTTCTGTGCGAGGTATGGTAAGTTC
GGCGAAATGGACTACTGGGGTCAAGGAACCTCAGTCACCGTCTCCTCA Light Chain:
ATTGTGATGACACAATCTCCAGCTTCTTTGGCTGTGTCTCTGGGGCAGAGG
GCCACCATCTCCTGCAGATCCAGTGAAACTGTTGATAGTGATGGCAATAGT
TTTATGCACTGGTACCAGCAGAAACCAGGACAGTCACCCAAACTCCTCTTG
TATCTTGCATCCACCCTAGAATCTGGGGTCCCTGCCAGGTTCAGTGGCAGT
GGGTCTAGGACAGACTTCACCCTCACCATTGATCCTGTGGAGGCTGATGAT
GCTGCAACCTATTACTGTCACCAAAATAATGAGGATCCGACGTTCGGTGGA
GGCACCAAGCTGGAAATCAAACGT

FIG. 5

```
                                  p35              calpain cleavage site
     MGTVLSLSPS YRKATLFEDG AATVGHYTAV QNSKNAKDKN LKRHSISIS̲V̲L̲   50
     PWKRIVAVSA KKKNSKKAQP NSSYOSNIAH LNNENLKKSL SCANLSTEAQ  100
     PPPAQPPAPP ASQLSGSQTG VSSSVKKAPH PAITSAGTPK RVIVQASTSE  150
     LLRCLGEFLC RRCYRLKHLS PTDPVLWLRS VDRSLLLQGW QDQGFITPAN  200
p10
     VVFLYMLCRD VISSEVGSDH ELQAVLLTCL YLSYSYMGNE ISYPLKPFLV  250
p25
     ESCKEAFWDR CLSVINLMSS KMLQINADPH YFTQVFSDLK NESGQEDKKR  300
     LLLGLDR 307
```

FIG. 7A

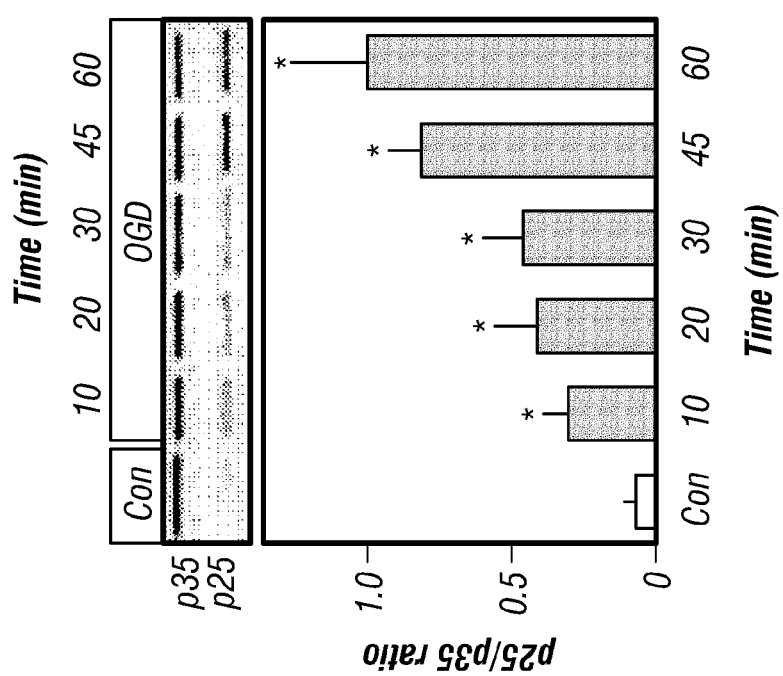
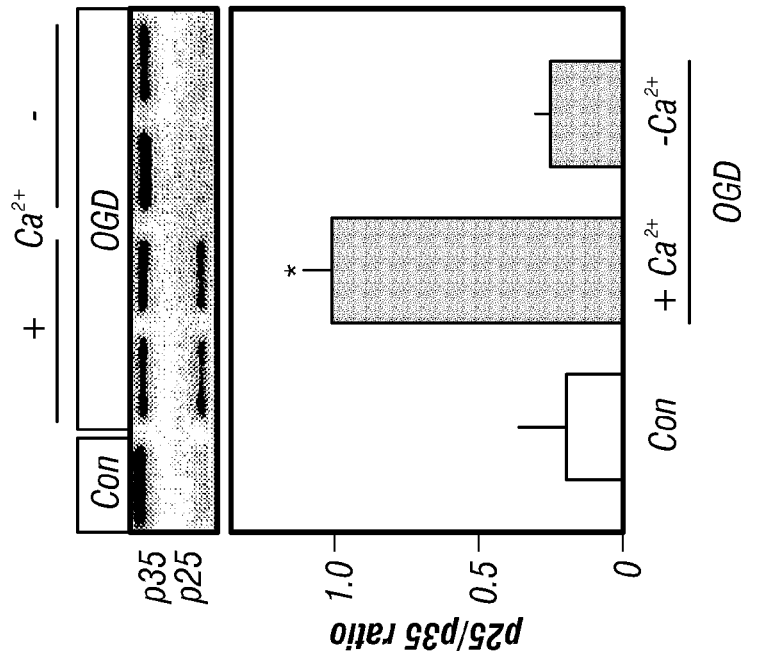
FIG. 8B
FIG. 8A

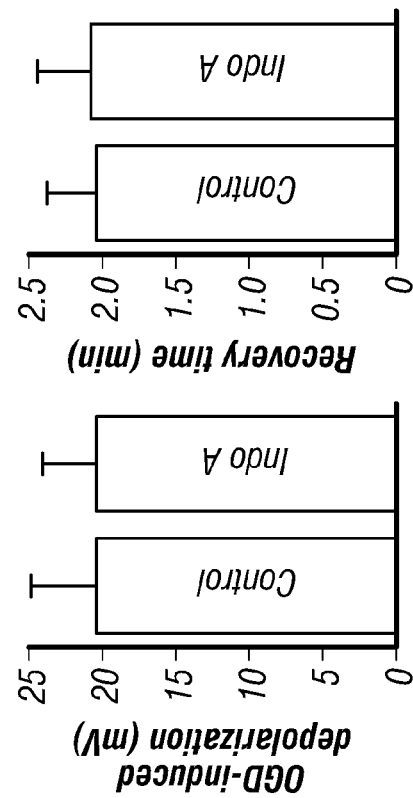
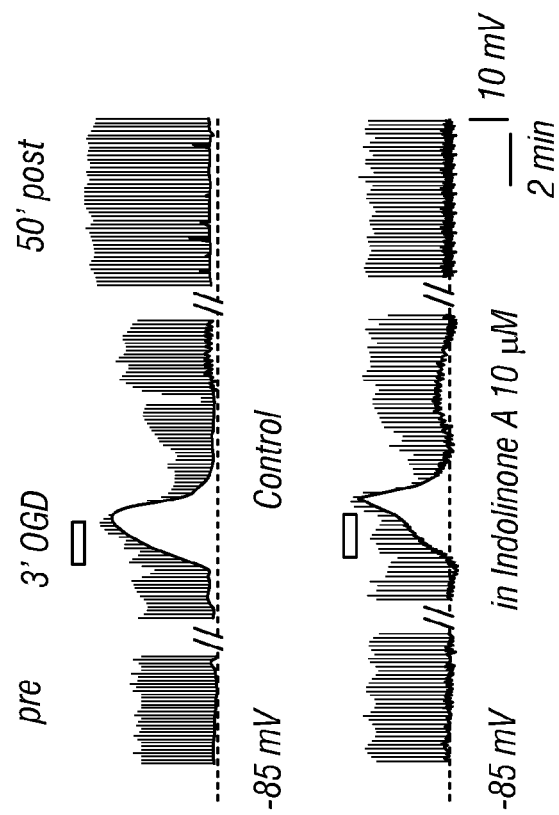
FIG. 10B
FIG. 10A

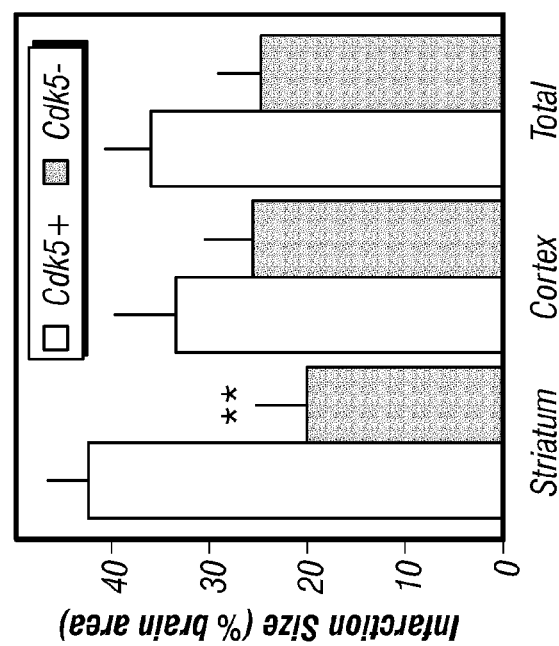
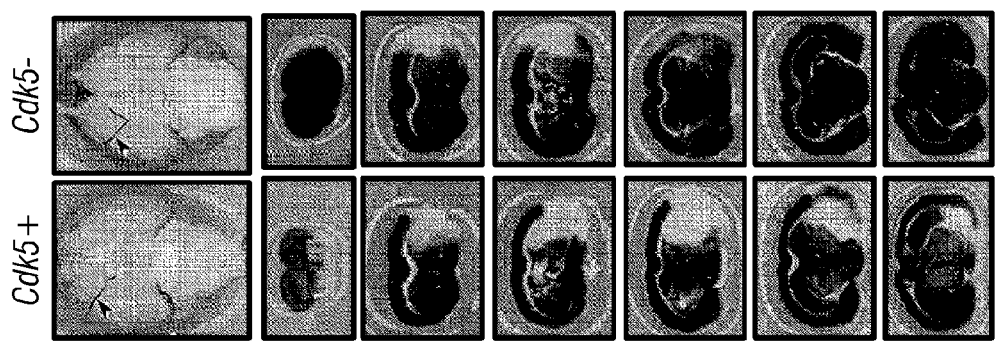
FIG. 11B

ANTIBODIES THAT BIND SELECTIVELY TO P25 AND USES THEREFOR

This application is a national phase application under 35 U.S.C. §371 of International Application No. PCT/US2010/037243 filed Jun. 3, 2010 which claims benefit of priority to U.S. Provisional Application Ser. No. 61/183,694, filed Jun. 3, 2009, the entire contents of each of these applications are hereby incorporated by reference.

This invention was made with government support under R01 DA016672-01 awarded by NIH (National Institute of Drug Abuse). The government has certain rights in the invention.

BACKGROUND OF THE INVENTION

I. Field of the Invention

The present invention relates to a monoclonal antibody or fragment thereof that can recognize the aberrant form of the Cdk5 activator, p25 but not p35, which is the physiologically active form of the activator. It further relates to the hybridoma cell line, which produces the monoclonal antibody and a method of producing the antibody or fragment thereof as a recombinant protein. The invention also relates to methods for the detection and isolation of p25 or homologs thereof from biological specimens. Furthermore, the invention relates to the use of the monoclonal antibody or fragment thereof for the detection and treatment of neuronal disorders and cancer.

II. Description of Related Art

Cognitive impairment due to dementia constitutes a major symptom in patients suffering from neurodegenerative diseases such as Alzheimer's disease, vascular dementia, mixed dementia, and Parkinson's disease. Alzheimer's disease, which accounts for approximately half of all dementia cases, afflicts over 5.1 million Americans. Without additional therapeutics, it is estimated that by 2050, 11 to 16 million patients will suffer from Alzheimer's disease. Major neuropsychiatric disorders including attention deficit hyperactivity disorder (ADHD) and post-traumatic stress disorder (PTSD) also involve disorders in cognition and aversive memory.

Aberrant Cdk5 activity, resulting from the cleavage of p35 into p25, has been implicated in Alzheimer's disease (AD), tauopathies, Parkinson's disease, amyotrophic lateral sclerosis, Huntington's disease, and Niemann-Pick disease. Cdk5 in this form associates with and contributes to the formation of neurofibrillary tangles (NFT) associated with AD brain neuropathology. Cdk5 phosphorylates the neurofilament-associated protein, tau as well as other cytoskeletal components. Dysregulation of Cdk5 results in hyperphosphorylation of tau and Cdk5 has also been found to phosphorylate the Alzheimer's precursor protein (APP). Overexpression of p25 in the cortex and hippocampus results in increased phospho-tau levels, NFT formation, and neurodegeneration. Aberrant Cdk5 activity has also been associated with hippocampal sclerosis and epilepsy, retinal degeneration, pain, and spinal chord injury.

Calpain-dependent p25 generation in response to hypoxia, ischemia, and stroke, contributes to the resulting neuronal cell loss, and Cdk5 inhibitors have been shown to mitigate cerebral tissue damage induced by stroke. Induction of aberrant Cdk5 activity has been shown to be the mode of action of numerous neurotoxic agents. Calpain cleavage of p35 occurs in response to neurotoxic insult and contributes to the neuronal cell death induced by MPTP, Aβ, maitotoxin, MPTP, organophosphates, and very low levels of methylmercury. Dysregulation of Cdk5 may also mediate the deleterious effects of the neurotoxins methamphetamine, 6-hydroxydopamine, quinolinic acid and kainic acid. Because aberrant Cdk5 activity has been so widely implicated in neurotoxicity and neurological and neurodegenerative disorders, it has been recognized as a therapeutic target for neurodegenerative disorders. However, the ability to examine the role of Cdk5 in these diseases has been hampered by the absence of a reagent that can selectively identify the Cdk5/p25 complex. Indeed, until now, the difference in the normal Cdk5/p35 complex and the disease causing Cdk5/p25 complex has been viewed as too subtle to permit differentiation of the two.

Interestingly, in a recent study it was found that overexpression of p25 in the motor control and reward center of the brain, the striatum did not result in immediate neuronal cell death but caused loss of synaptic circuitry (dendritic spines) neuroinflammation, comprised dopamine-mediated signal transduction, and impairments of dopamine-mediated behavior and motor learning (Meyer et al., 2008). Thus, neurological and neuropsychiatric disorders that may not be solely limited to neurodegeneration may arise from p25 generation. It should be noted that while the neurotoxicity and harmful effects of p25 are very well demonstrated, it can not be ruled out that the generation of low levels of p25 during strong excitotoxic excitatory glutamatergic neurotransmission may have a physiological function. One possibility is that it may recruit mitochondria in the synapse although this is only speculation at this point. Furthermore, overexpression of p25 in the parafollicular cells of the thyroid resulted in aggressive, 100% lethal medullary thyroid carcinoma, suggesting that Cdk5 and p35 or p25 are oncogenic and may be important contributors to neuroendocrine and other forms of cancer.

For research, diagnostic and pharmaceutical studies, there is a need for antibodies that selectively recognize p25, but not p35. To date, there have been no reports of such an antibody. Commercially available polyclonal antibodies to p35 also recognize p25, while there are no commercially available monoclonal antibodies to either p35 or p25. Polyclonal antibodies, although widely used, have the disadvantage in that they are of limited availability and can no longer be reproduced after the initial production. Additionally, polyclonal antibodies are a mixture of antibodies, which recognize different antigenic epitopes, and therefore it is not possible to reproduce polyclonal antibodies that recognize the same antigenic structures. Therefore, there is a need for monoclonal antibodies, which selectively and reproducibly detect p25 and not p35 thereby allowing the identification of aberrant Cdk5 activity associated with neurodegenerative diseases and cancers.

SUMMARY OF THE INVENTION

Thus, in accordance with the present invention, there is provided a monoclonal antibody or fragment thereof that binds to p25 but does not bind to p35. The antibody or fragment may be produced by the hybridoma cell line 1C4 deposited with the ATCC as PTA-8555. The antibody or fragment may be a recombinant antibody or fragment. Also provided is a hybridoma that expresses an antibody that binds to p25 but does not bind to p35, including a hybridoma cell line is 1C4 and deposited with the ATCC as PTA-8555.

A method of selectively detecting p25, a p25 fragment or homolog thereof in a tissue or fluid comprising (a) providing a biological tissue or fluid; (b) contacting said tissue or fluid with an antibody or fragment thereof that binds to p25 but does not bind to p35; and detecting p25, a p25 fragment or homolog thereof in said tissue or fluid bound to said antibody. The p25, p25 fragment or homolog thereof in the biological sample may be isolated by association with said antibody or fragment thereof which is fixed to a solid phase. The tissue may be from a human biopsy, or located in a living human.

The human tissue or fluid may be from a subject known to have or suspected of having a neurodegenerative disease, such as Alzheimer's Disease, Parkinson's Disease, Niemann-Pick Disease, amyotrophic lateral sclerosis, Huntington's Disease, or hippocampal sclerosis. The method may further comprising making a diagnosis of a neurodgenerative disease based on the results of step (c). The method further may comprise making a treatment decision based on the results of step (c). In addition, the method may further comprising treating said subject with a neurodegenerative disease therapy, and may further comprise performing steps (a)-(c) a second time. The method may also further comprise making a prognosis based on the results of step (c) from the first and second performing of steps (a)-(c), and the subject may have received neurodegenerative disease therapy between said first and second performing of steps (a)-(c).

The human tissue or fluid may be from a subject know to have or suspected of having suffered a neuronal injury or insult, such as hypoxia, ischemia, stroke, retinal degeneration, epilepsy, cerebral palsy, myocardial infarction, or spinal chord injury. The method may further comprise making a treatment decision based on the results of step (c). The method may further comprise treating said subject with a neuronal therapy. The method may further comprise performing steps (a)-(c) a second time, and may further comprise making a prognosis based on the results of step (c) from the first and second performing of steps (a)-(c). The subject may have received neurodegenerative disease therapy between said first and second performing of steps (a)-(c). The method may also further comprising making a diagnosis of a neuronal injury or insult based on the results of step (c).

The human tissue or fluid may be from a subject known to have or suspected of having cancer. The method may further comprise making a treatment decision based on the results of step (c). The method may further comprising treating said subject with a cancer therapy. The method may further comprise performing steps (a)-(c) a second time. The method may further comprise making a prognosis based on the results of step (c) from the first and second performing of steps (a)-(c), and the subject may have received cancer therapy between said first and second performing of steps (a)-(c). The method may further comprise making a diagnosis of cancer type based on the results of step (c).

In still another embodiment, there is provided a method of treating a disease state in a subject involving aberrant Cdk5 activity comprising administering to said subject an antibody or fragment thereof that binds to p25 but does not bind to p35. The subject may be known to have or suspected of having a neurodegenerative disease, such as Alzheimer's Disease, Parkinson's Disease, Niemann-Pick Disease, amyotrophic lateral sclerosis, Huntington's Disease, or hippocampal sclerosis, known to have or suspected of having suffered a neuronal injury or insult, such as hypoxia, ischemia, stroke, retinal degeneration, epilepsy, cerebral palsy, myocardial infarction, or spinal chord injury, or known to have or suspected of having cancer. The method may further comprise administering said antibody or fragment a second time.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Purified Cdk5/p25 subjected to SDS-PAGE and staining with Coomassie Brilliant Blue (left) or immunoblotting with anti-Cdk5 monoclonal antibody 1H3 (middle) or anti-p25 monoclonal antibody 1C4 (right) is shown. (FIG. 2B) Immunoblots of striatal homogenates from p25 overexpression mice (p25OE) (100 µg) with a commercial antibody (C-19) or monoclonal antibody 1C4 is shown. (FIG. 2C) Immunohistochemical stains of HEK293T cells transfected with the indicated expression vectors (right) using the indicated antibodies (top).

(FIG. 3A) Specific detection of ischemic damage induced by selective embolic right middle cerebral artery occlusion (MCAO, unilateral induced stroke, left side) with no damage detected in the unstroked hemisphere (right) of the same rat brain. The boxes mark damaged areas. The top panel (red) shows staining of the striatum with the p25 monoclonal antibody and the lower panel (green) shows the same brain region stained with GFAP (a marker for neuronal damage). (FIG. 3B) Selective detection of p25 in striatal primary cultures subjected to ischemic conditions (i.e., oxygen and glucose deprivation, OGD). Cells were transfected with lentivirus expressing GFP, which is used as a co-stain in the top panels (green). Bottom panels (red) show p25 staining in cells under oxygenated conditions (left) and in response to ischemia (OGD, right).

FIG. 4—Inhibition of Cdk5/p25 but not PKA by monoclonal antibody 1C4. A curve is shown for the inhibition of Cdk5 by 1C4. Note, that it almost completely inhibits Cdk5 activity but has no effect on PKA.

FIG. 5—DNA sequence of monoclonal antibody 1C4. The heavy (SEQ ID NO: 1) and light (SEQ ID NO: 2) chains of the monoclonal antibody are shown.

(FIG. 6A) Quantitation of mortality for p25OE mice and liter mate controls is shown (n=28). (FIG. 6B) Dissection showing thyroid tumors in a p25OE mouse (arrows) versus a liter mate control. (FIG. 6C) Immunoblots showing the detection of p25-GFP (using anti-GFP antibody) and Cdk5 in thyroid lysates from control and p25OE (tumor) mice.

FIGS. 7A-E—p25 is generated in rat striatum by stroke. (FIG. 7A) p35/p25 amino acid sequence (SEQ ID NO: 3). (FIG. 7B) Quantitative immunoblots of p35/p25 in three regions of control and stroked brain hemispheres at various periods after unilateral MCAO. Data represent means±s.e.m. (FIG. 7C), Immunostains of rat striatum from control and stroked hemispheres (6 h after MCAO) for p35 and DARPP-32. (FIG. 7D) Staining of stroked hemispheres 6 h after reperfusion for p25, Fluorojade B and 24 h after reperfusion for GFAP. (FIG. 7E) GFP and p25 detection in costained GFP-expression vector-transfected primary cultured striatal neurons before and after OGD. Scale bars=2 mm (low magnification) and 100 μm (FIG. 7D) and 25 μm (FIGS. 7C and 7E).

FIGS. 8A-F—Inhibition of Cdk5 prevents neuronal cell death from ischemia in acute brain slices. (FIG. 8A) Time-dependent p25 generation in striatal slices in response to OGD. (FIG. 8B) Attenuation of OGD-induced p25 generation by $Ca^{2+}$ removal. (FIG. 8C) Inhibition of OGD-dependent p25 generation by calpain inhibitors calpeptin (Cpn, 20 μM) or calpain inhibitor 3 (CI3, 20 μM). (FIG. 8D) Dose-response inhibition of Cdk5 by Indo A, as assessed by blotting phospho-Thr75 DARPP-32 (D32). (FIG. 8E) Viability staining (TTC) of coronal slices after 30 or 60 min of OGD in the absence or presence of calpeptin or Indo A. (FIG. 8F) Quantitation of the effects of calpeptin, Indo A, or Indo B on viability. Data represent means±s.e.m. *$p<0.05$ (Student's t-test) compared to control. #$p<0.05$ vs. same period of OGD treatment alone.

(FIGS. 9A-B) Effect of 20 min OGD/10 min reperfusion on phospho-Ser845 GluR1 (FIG. 9A) and phospho-Thr34 DARPP-32 (FIG. 9B) in response to SKF81297 (SKF, 1 μM, 5 min). (FIG. 9C) Effect of 0, 3, or 10 min OGD/10 min reperfusion on stimulation of phospho-Ser845 GluR1 by SKF81297 in the absence or presence of Indo A, (1 h, 10 μM). Data represent means±s.e.m. *$p<0.05$ (Student's t-test) vs. control.

FIGS. 10A-F—Inhibition of Cdk5 prevents the induction of i-LTP and attenuates ischemia-induced FP loss. (FIG. 10A) Effect of 3 min OGD on membrane potential and EPSP amplitude (upward deflections) in control (top) and Indo A-treated striatal slices (bottom). Note the lack of increase in EPSP amplitude 50 min post-OGD in the Indo A-treated slice relative to pre-OGD conditions. (FIG. 10B) Mean OGD-induced depolarization amplitude (white bars) and mean recovery-time (grey bars) of medium spiny neurons after 3 min OGD in untreated and Indo A-treated slices. (FIG. 10C) Single tracings show the EPSP amplitude 5 min before, during, and 50 min after OGD in control and Indo A-treated slices. (FIG. 10D) Time-course of EPSP amplitudes revealing i-LTP after 3 min OGD (Control). The i-LTP is abolished by Indo A. (FIG. 10E) Tracings show FPs 5 min before, during and 50 min after OGD in control and in Indo A-treated slices. (FIG. 10F) The plot shows the effect of 10 minutes of OGD on the time-course of FP amplitudes recorded in control and Indo A-treated slices. Data represent means±s.e.m.

FIGS. 11A-B—Cdk5 CKO is neuroprotective against ischemia and stroke. (FIG. 11A) TTC staining of striatum from Cdk5+ (WT) or Cdk5-(CKO) mice subjected to the indicated period of OGD, is shown with quantitation. *$p<0.05$, $p<0.01$ compared to 0 OGD control; #$p<0.05$, ##$p<0.01$ (Student's t-test) compared to same treatment for Cdk5+, n=6. (FIG. 11B) TTC stained coronal brain sections from Cdk5+ or Cdk5− mice after MCAO (2 h), reperfusion, and 48 h survival. The top panel depicts ventral view of brains from Cdk5+ and Cdk5− littermates showing a representative embolism of the MCA (arrows) verifying placement. Quantitation of infarct size is shown (right). Data represent means±s.e.m. $p<0.01$, *$p<0.05$, ANOVA with Bonferroni's post hoc, n=9 for each group.

DESCRIPTION OF ILLUSTRATIVE EMBODIMENTS

Figure 1:
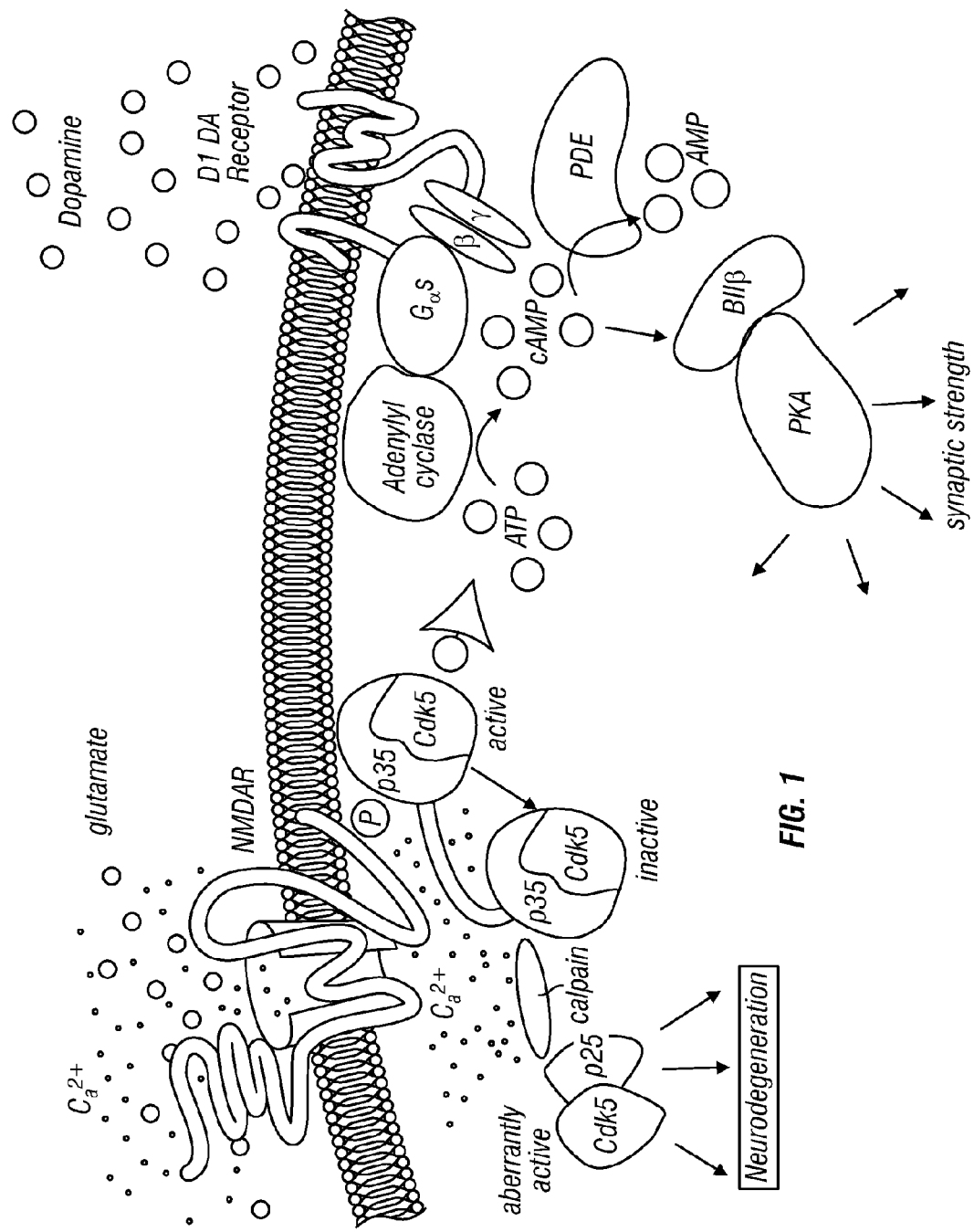
FIG. 1—Schematic model of normal and aberrant Cd5 generation, and downstream effectors.
Figure 2A:
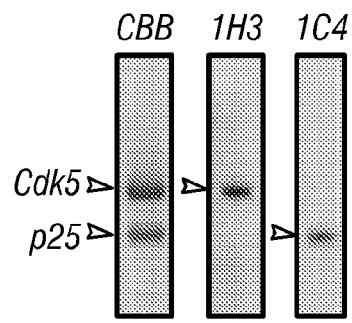
FIGS. 2A-C—Generation of monoclonal antibodies specific for Cdk5 and p25.
Figure 2B:
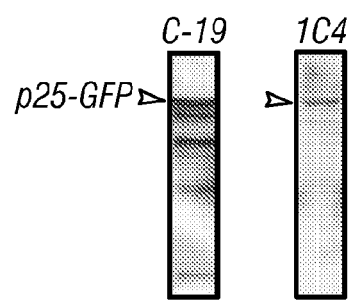
Figure 2C:
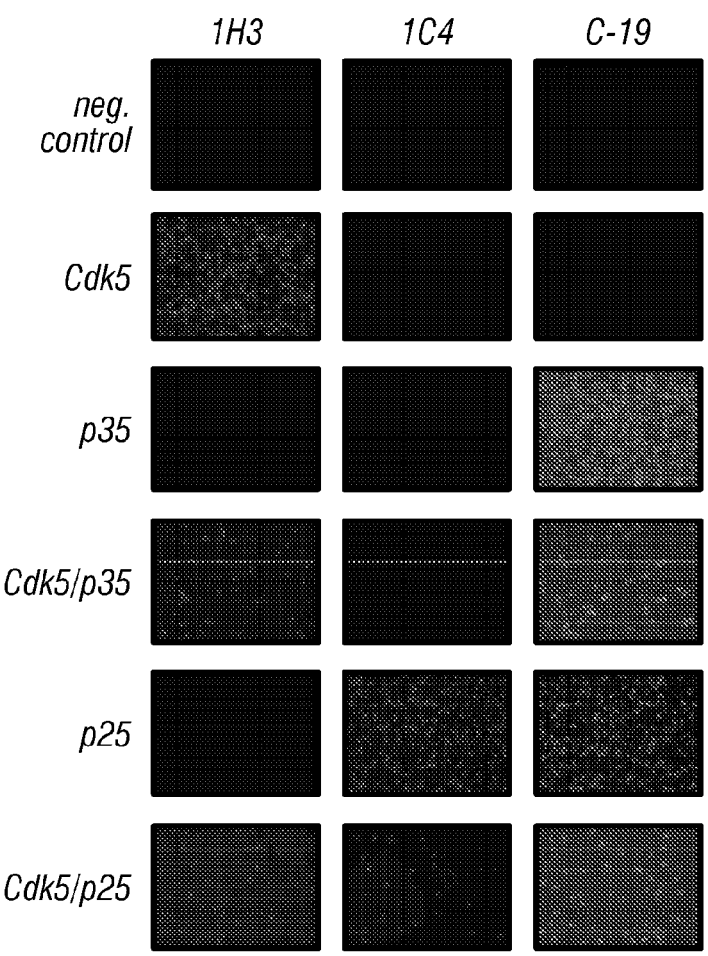
Figure 3A:
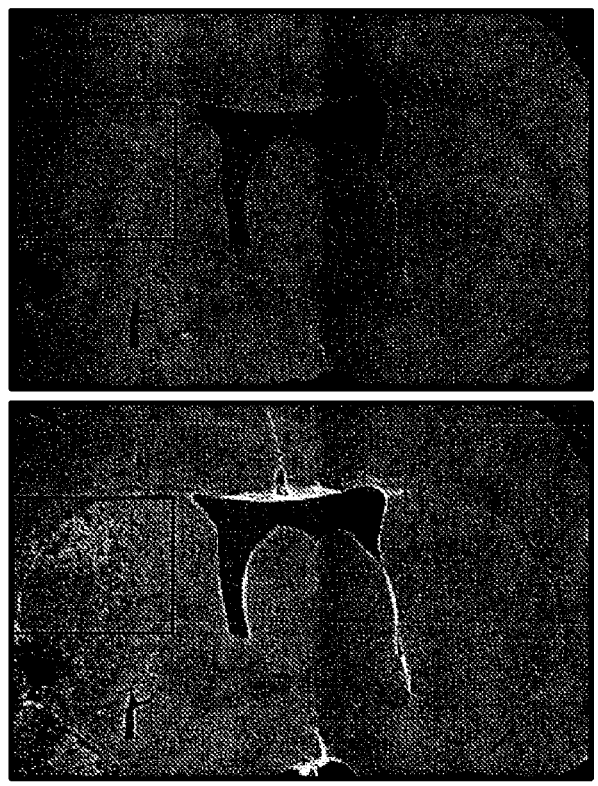
FIGS. 3A-B—Detection of ischemia-induced neurodegeneration by the p25 monoclonal antibody.
Figure 3B:
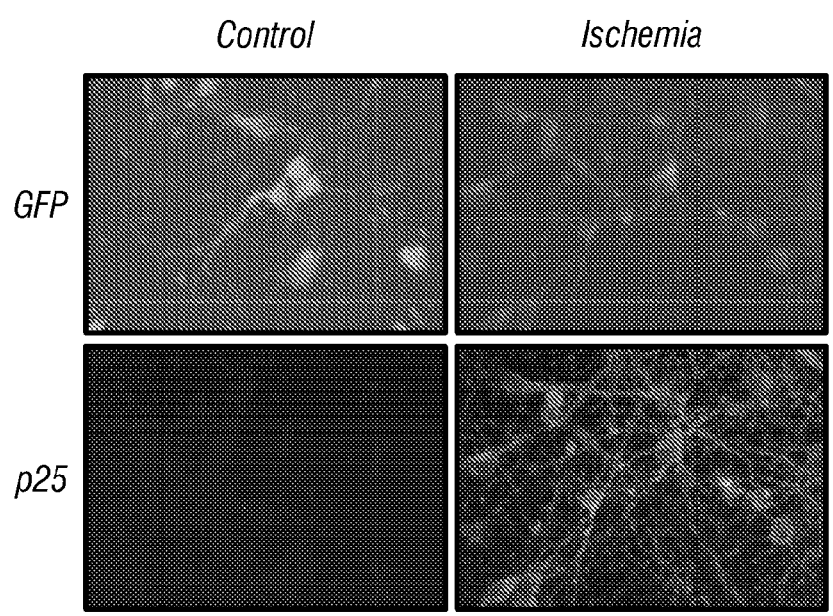

The inventors now provide new monoclonal antibodies that selectively and specifically recognize only the aberrant form of the Cdk5 cofactor p35, designated p25. p25 is produced in stressed neurons through the cleavage of the cofactor p35 by the calcium-dependent protease calpain (FIG. 1). The resulting Cdk5/p25 complex is aberrantly active and causes neurodegeneration. The new monoclonal antibody produced detects p25 production that accompanies neurodegeneration. It has been used to detect p25 expression by immunoblotting (FIGS. 2A-B). The antibody only stains cells transfected with a plasmid expressing p25, but not p35 or Cdk5 (FIG. 2C). FIGS. 3A-B demonstrate the ability of this new monoclonal antibody to selectively and specifically detect tissue damaged by stroke, and p25 generation in striatal neuron primary cultures subjected to ischemia. Thus, it constitutes an important new diagnostic and prognostic reagent.

Figure 6A:
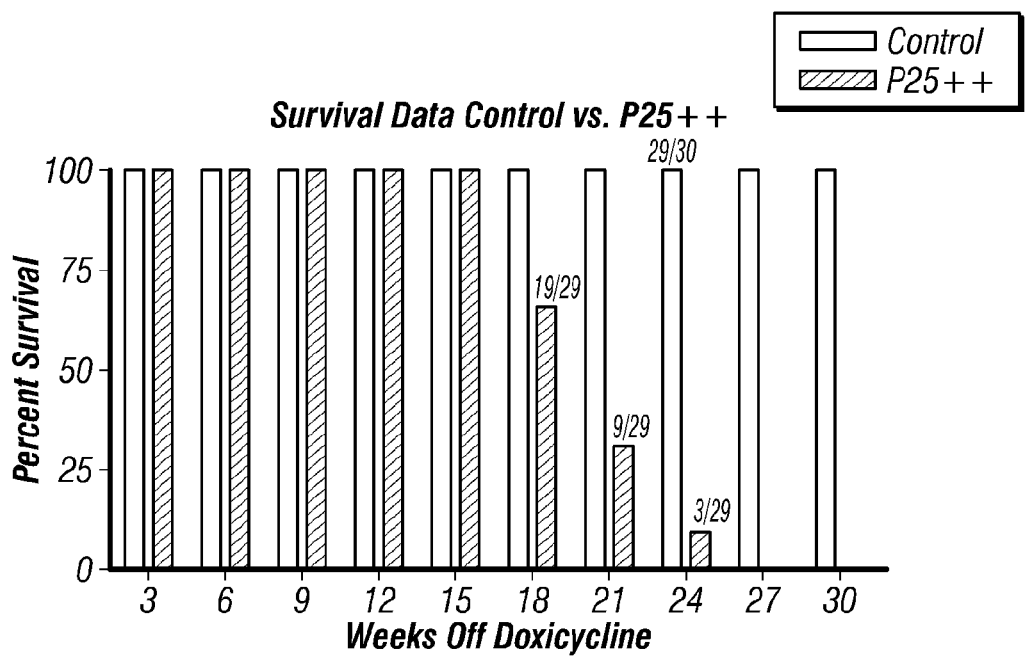
FIGS. 6A-C—p25 overexpression (p25OE) results in mortality and thyroid tumors.
Figure 6B:
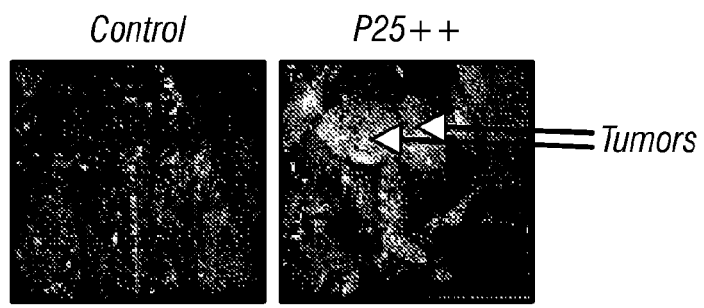
Figure 6C:
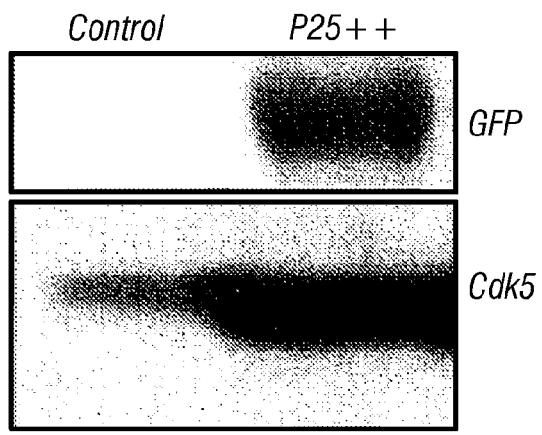

In addition, the inventors have found that this monoclonal antibody selectively inhibits the activity of the aberrant form of Cdk5/p25 (FIG. 4), indicating it also has therapeutic activity in the prevention of prevent neuronal cell death and neurodegeneration. Furthermore, the inventors have found that the overexpression of p25 in mice results in medullary thyroid carcinomas and death (FIGS. 6A-B). However, inhibition of Cdk5 or p25 expression attenuated tumor growth, implicating Cdk5 activity in oncogenesis. In addition, the inventors' data suggests the basis of this antibody's specificity is due to a modification that distinguishes the form of p25 copurified with kinase-dead Cdk5 from that isolated with the active enzyme. Based on this information, it is clear that this antibody is an important new diagnostic, prognostic and therapeutic tool.

I. Cdk5 AND p35/p25

Cdk5 is an atypical member of the cyclin-dependent kinase family that is dependent upon association with the neuronal specific cofactor p35 for activation. It is constitutively active in neurons and is involved in many aspects of neuronal function including corticogenesis (Ohshima et al., 1996), neuromuscular junction formation (Cheung et al., 2006), the synaptic vesicle cycle (Nguyen & Bibb, 2003; Sahin & Bibb, 2004), and dopamine neurotransmission (Bibb, 2003; Bibb et al., 1999; 2001a). It has also been implicated in virtually every form of neurotoxicity and neurodegeneration (Cruz & Tsai, 2004; Guo, 2003). This dual role in health and disease is conferred upon Cdk5 by virtue of the fact that p35 serves as a substrate of the $Ca^{2+}$-dependent protease, calpain (Kusakawa et al., 2000).

Under stressful conditions, calpain is activated by elevated intracellular $Ca^{2+}$ and cleaves p35, thereby removing the first 100 amino acids to produce p25 (Lee et al., 2000) (FIG. 1). Cdk5 associated with p25 phosphorylates aberrant substrates leading to cell death. Interestingly, before transgenic overexpression of p25 causes neurodegeneration, it results in a transient improvement in learning and synaptic plasticity (Cruz et al., 2003; Fischer et al., 2005). Using the anti-p25 antibody described herein, the inventors have recently found that low levels of p25 are generated at the synapse by physiological glutamatergic neurotransmission. Cdk5 has been suggested to be an important regulator of synaptic plasticity, learning and memory (Angelo et al., 2006), but the mechanisms by which it contributes to this most fundamental feature of brain function have, until now, been unclear.

II. ANTIBODIES AND METHODS OF GENERATION

The techniques to produce antibodies, including monoclonal antibodies, are well known to those of skill in the art. For example, the hybridoma method first described by Kohler & Milstein (1975) is still in use today. Recombinant DNA methods (U.S. Pat. No. 4,816,567) also have been described. Additionally, it is within the scope of the invention to produce fragments of the antibody, which retain the antigen binding function of the antibody and are segments of the antibody such as $F_{as}$, $F_{(ab')2}$, $F_v$ and other fragments that can for example be produced as recombinant proteins.

A unique anti-p25 antibody-producing hybridoma cell line, designated 1C4, was deposited with ATCC, Manassas, Va., on Jul. 30, 2007 (accession no. PTA-8555).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Myeloma cells that fuse efficiently, support stable highlevel expression of antibody by the selected antibody-producing cells, and are sensitive to a medium such as HAT medium are selected for use with these methods. Among these are murine myeloma lines, such as those derived from MOPC-21 and MPC-11 mouse tumors available from the Salk Institute Cell Distribution Center, San Diego, Calif. USA, and SP-2 cells.

Culture medium in which hybridoma cells are growing is assayed for production of monoclonal antibodies directed against the antigen of interest. The binding specificity of antibodies produced by hybridoma cells may determined by immunoprecipitation, or by in vitro binding assays such as radioimmunoassay (RIA) or enzyme-linked immunoabsorbent assay (ELISA). The binding affinity of the monoclonal antibody can, for example, be determined by the Scatchard analysis of Munson & Pollard (1980).

After hybridoma cells are identified that produce antibodies of the desired specificity, affinity, and/or activity, the clones may be subcloned by limiting dilution procedures and grown by standard methods (Goding, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones may be suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies or fragments thereof in the recombinant host cells.

The DNA also may be modified, for example, by substituting the coding sequence for human heavy and light chain constant domains in place of the homologous murine sequences, Morrison et al. (1984), or by covalently joining to the immunoglobulin coding sequence all or part of the coding sequence for a non-immunoglobulin polypeptide. In that manner, "chimeric" or "hybrid" antibodies are prepared that would have the binding specificity of an anti-p25 monoclonal antibody herein. Typically such non-immunoglobulin polypeptides are substituted for the constant domains.

Chimeric or hybrid antibodies or fragments thereof also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies or fragments thereof of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, β-galactosidase or horseradish peroxidase.

Any method known in the art for separately conjugating the antibody or fragment thereof to the detectable moiety may be employed, including those methods described by Hunter et al. (1962); David et al. (1974); Pain et al. (1981); and Nygren (1982).

The antibodies or fragments thereof of the present invention may be employed in any known assay method, such as competitive binding assays, direct and indirect sandwich assays, and immunoprecipitation assays. See Zola (1987).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Humanized antibodies have several advantages for human therapy including not being recognized as foreign antibodies, remaining in the human circulation system with half-lives similar to human antibodies, and interacting better with the human immune system to destroy antigenic cells by the compliment-dependent and antibody-dependent cellular cytotoxicity systems.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

Human monoclonal antibodies can be made by the hybridoma method. Human myeloma and mouse-human heteromyeloma cell lines for the production of human monoclonal antibodies have been described, for example, by Kozbor (1984), and Brodeur et al. (1987).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al. (1993a); Jakobovits et al. (1993b).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson and Chiswell (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library is reported by Griffith et al. (1994). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e., the epitope governs (imprints) the choice of partner. When the process is repeated in order to replace the remaining rodent V domain, a human antibody is obtained (WO 93/06213). Unlike traditional humanization of rodent antibodies by CDR grafting, this technique provides completely human antibodies, which have no framework or CDR residues of rodent origin.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. For further details of generating antibodies with modified binding specificities, for example, Suresh et al. (1986).

Monoclonal antibodies are large molecules, which are difficult to make. However, their ability to identify very specific targets makes them appealing as markers of neurodegeneration and cancer therapies. Smaller antibody fragments and engineered variants which retain or enhance the specificity of the whole monoclonal antibody are emerging as therapeutic tools against numerous diseases. Therefore, more recent studies have focused on the use of monoclonal antibodies or fragments thereof as delivery systems to target drugs, toxins, peptides, proteins, radionuclides or viruses to specific sites. For example, cancer therapy, antibodies are engineered to target tumor-associated antigens and deliver a cytotoxic payload. Antibody fragments fused to lipids, forming liposomes loaded with cytotoxins or vaccines, can target peripheral tissues and brain tumors since liposomes can cross the blood-brain barrier. Yet another use is as a delivery system by the fusion of enzymes to the fragment, which can then serve to activate drugs in cancer and tumors therapies, or block cellular receptors and prevent cell proliferation. For example, in antibody-directed enzyme prodrug therapy (ADEPT), the monoclonal antibody-enzyme conjugate recognizes and binds to specific antigens on the surface of a tumor. When the cytotoxic agent is delivered in an inactive form (prodrug), the enzyme conjugated to the monoclonal antibody cleaves the inactivating sequence and multiple copies of the active drug are released within the tumor environment.

III. DIAGNOSTIC METHODS

As discussed above, the present disclosure also provides for the use of p25-selective antibodies in the detection of p25 and Cdk5/p25 complexes in diseased subjects and biological samples therefrom. In particular, neurodegenerative diseases such as Alzheimer's Disease, Parkinson's Disease, Niemann-Pick Disease, amyotrophic lateral sclerosis, Huntington's Disease, and hippocampal sclerosis and certain cancers may be diagnosed and/or monitored using immunoassays, as described below.

Samples may be obtained from subjects that either have or are suspected of having a neurodegenerative disease or cancer. Samples may be obtained through biopsies, collection of bodily fluids such as spinal fluid, urine, or blood, and post-mortem autopsies. Biopsies can be used to obtain tissue from bone marrow, breast tissue, cervix, kidney, liver, lymph nodes, lungs, thyroid, prostrate, intestine, skin, adrenal gland, heart etc. Such tissue can then be screened with the monoclonal antibody and positive results may indicate cancerous states of the tissue. Additionally, biological fluids may be screened for abnormal levels of p25, which may indicate cancers in the cases of urine or blood screens, or neurodegeneration in the case of spinal fluid screening. Post-mortem brain tissue may be screened with the p25 monoclonal antibody to determine regions of the brain affected by neurological diseases.

Immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999), Gulbis and Galand (1993), De Jager et al. (1993), and Nakamura et al. (1987).

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody or fragment thereof employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody or fragment thereof, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Enzyme-linked immunosorbent assays (ELISAs) utilize antibodies to detect one or both members of a complex (e.g., Ckd5, p25 and Cdk5/p25), homologs and fragments of proteins, as well as novel proteins associated with the complex. Antibodies binding to one member of the complex may be immobilized onto a selected surface exhibiting protein affinity, such as a well in a polystyrene microtiter plate. Then, a composition having the antigen(s) is added to the wells. After binding and washing to remove non-specifically bound immune complexes, the bound antigen(s) may be detected. Detection may be achieved by the addition of a labeled antibody directed to the second member of the complex. This type of ELISA is a simple "sandwich ELISA." Detection may also be achieved by the addition of a third labeled antibody that binds the second antibody. Other formats may be applied as well.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

IV. TREATMENTS

1. Neurodegenerative Diseases

Neurodegenerative Diseases (NDs) include a wide variety of debilitating afflictions of the central and peripheral nervous systems. Most, however, affect the CNS. Such diseases include Alzheimer's Disease, Pick's Disease, senile dementia, Parkinson's Disease, multiple sclerosis, multiple system atrophy, dementia with Lewy bodies, Huntingon's Disease, Progressive Supranuclear Palsy, Creutzfeldt-Jakob Disease, amyotrophic lateral sclerosis, dementia, motor neuron disease, prion disease, Huntington's disease, Tauopathies, Chromosome 17 dementias, hereditary neuropathies, and diseases involving cerebellar degeneration.

A. Parkinson's Disease

Parkinson's Disease (PD) is one of a group of conditions classified as movement disorders. It is both chronic and progressive. Parkinson's disease occurs when cells of the substantia nigra begin to malfunction and eventually die. This results in the loss of dopamine production, a chemical messenger that transports signals to the parts of the brain that control movement initiation and coordination. The primary symptoms are tremors, rigidity or stiffness of the limbs and trunk, bradykinesia or slowness of movement, and postural instability or impaired balance and coordination. Secondary symptoms included speech changes, loss of facial expression, difficulty swallowing, drooling, pain, dementia or confusion, sleep disturbances, depression, fear or anxiety, memory difficulties, urinary problems, fatigue and aching, and loss of energy. However, symptoms vary, and the disease progression may be rapid or not.

Upwards of one million Americans suffer from PD. While approximately 15% of patients are diagnosed before the age of 40, incidence increases with age. The cause is unknown, and although there is presently no cure, there are many treatment options such as medication and surgery to manage the symptoms. The degree of success of each treatment varies among individuals, as does the length of time the treatment option remains effective.

Levodopa is a dopamine precursor, which was considered a breakthrough in the treatment of PD. Unfortunately, patients experienced debilitating side effects, including severe nausea and vomiting, and with increased dosing and prolonged use, patients experienced other side effects including dyskinesias. Sinemet (Levodopa+Carbidopa) represented a significant improvement in that the addition of carbidopa prevents levodopa from being metabolized in the gut, liver and other tissues, allowing more of it to get to the brain. Thus, a smaller dose of levodopa is needed, and the severe nausea and vomiting was greatly reduced.

Stalevo (carbidopa+levodopa+entacapone) is combination tablet for patients who experience signs and symptoms of end-of-dose "wearing-off." The tablet combines carbidopa/levodopa with entacapone. While carbidopa reduces the side effects of levodopa, entacapone extends the time levodopa is active in the brain (up to 10% longer).

Symmetrel (amantadine hydrochloride) activates both the release of dopamine from storage sites, and possibly blocks the re-uptake of dopamine into nerve terminals. It also has a glutamate receptor blocking activity. Its dopaminergic actions result in its usefulness in reducing dyskinesia induced by levodopa and is thus called an indirect-acting dopamine agonist, and is widely used as an early monotherapy, and with the more powerful Sinemet added when needed.

Anticholinergics (trihexyphenidyl, benztropine mesylate, procyclidine, etc.) do not act directly on the dopaminergic system. Instead they act to decrease the activity of another neurotransmitter, acetylcholine. There is a complex interaction between levels of acetylcholine in the brain and levels of dopamine. Many clinicians find that if an agonist or levodopa does not relieve tremor, then the addition of an anticholinergic drug is often effective. Adverse effects include blurred vision, dry mouth and urinary retention. These drugs may be contraindicated in older patients since they can cause confusion and hallucination.

Other drugs include Selegiline or deprenyl (Eldepryl), which have has been shown to delay the need for Sinemet when prescribed in the earliest stage of PD. Dopamine agonists are drugs that activate dopamine receptors directly, and can be taken alone or in combination with Sinemet. Such agonists include bromocriptine (Parlodel), pergolide (Permax), pramipexole (Mirapex) and ropinirole (Requip). COMT inhibitors such as tolcapone (Tasmar) and entacapone (Comtan) prolong the duration of symptom relief by blocking the action of an enzyme which breaks down levodopa.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Surgery is an option for some patients after medications are no longer satisfactory. A patient should discuss surgery thoroughly with his or her neurologist before making any decision. Two older lesioning procedures are pallidotomy and thalamotomy. Pallidotomy can alleviate rigidity and bradykinesia symptoms, and thalamotomy helps to control tremors. Doctors rarely perform either procedure because both permanently destroy parts of the brain and have serious side effects. The damage could make it impossible to perform surgeries that may become available in the future, such as brain tissue transplants.

Deep brain stimulation (DBS) is safer and more effective, and thus has replaced these methods. It is a preferred surgical option because it has the same, if not better, results than pallidotomy and thalamotomy. DBS also leaves open the possibility of other therapies, should they become available in the future. As with any surgical procedure, there are risks and side effects. The main benefit of DBS surgery is to reduce motor fluctuations, i.e., the ups and downs caused by a decreasing effectiveness of Sinemet. The electrode is usually placed on one side of the brain. The DBS electrode implanted in the left side of the brain will control the symptoms on the right side of the body and vice versa. In some cases, patients will need to have stimulators on both sides of the brain.

B. Alzheimer's Disease

Dementia is a brain disorder that seriously affects a person's ability to carry out daily activities. Alzheimer's disease (AD) is the most common form of dementia among older people. Scientists believe that up to 4 million Americans suffer from AD. The disease usually begins after age 60, and risk goes up with age. While younger people also may get AD, it is much less common. About 3 percent of men and women ages 65 to 74 have AD, and nearly half of those age 85 and older may have the disease. While the subject of intensive research, the precise causes of AD are still unknown, and there is no cure.

AD attacks parts of the brain that control thought, memory and language. It was named after Dr. Alois Alzheimer, a German doctor. In 1906, Dr Alzheimer noticed changes in the brain tissue of a woman who had died of an unusual mental illness. He found abnormal clumps (now called amyloid plaques) and tangled bundles of fibers (now called neurofibrillary tangles). Today, these plaques and tangles in the brain are considered hallmarks of AD.

Scientists also have found other brain changes in people with AD. There is a loss of nerve cells in areas of the brain that are vital to memory and other mental abilities. There also are lower levels of chemicals in the brain that carry complex messages back and forth between nerve cells. Thus, AD may disrupt normal thinking and memory by inhibiting, both physically and chemically, the transfer of message between nerve cells.

AD is progressive, characterized by memory loss, language deterioration, impaired visuospatial skills, poor judgment, indifferent attitude, but preserved motor function. As mentioned, AD usually begins after age 65, but its onset may occur as early as age 40, appearing first as memory decline and, over several years, destroying cognition, personality, and ability to function. Confusion and restlessness may also occur. The type, severity, sequence, and progression of mental changes vary widely. The early symptoms of AD, which include forgetfulness and loss of concentration, can be missed easily because they resemble natural signs of aging. Similar symptoms can also result from fatigue, grief, depression, illness, vision or hearing loss, the use of alcohol or certain medications, or simply the burden of too many details to remember at once.

There is no cure for AD and no way to slow the progression of the disease. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. Also, some medications may help control behavioral symptoms such as sleeplessness, agitation, wandering, anxiety, and depression. These treatments are aimed at making the patient more comfortable.

The course of the disease varies from person to person. Some people have the disease only for the last 5 years of life, while others may have it for as many as 20 years. The most common cause of death in AD patients is infection.

The molecular aspect of AD is complicated and not yet fully defined. As stated above, AD is characterized by the formation of amyloid plaques and neurofibrillary tangles in the brain, particularly in the hippocampus which is the center for memory processing. Several molecules contribute to these structures: amyloid β protein (Aβ), presenilin (PS), cholesterol, apolipoprotein E (ApoE), and Tau protein. Of these, Aβ appears to play the central role.

Aβ contains approximately 40 amino acid residues. The 42 and 43 residue forms are much more toxic than the 40 residue form. Aβ is generated from an amyloid precursor protein (APP) by sequential proteolysis. One of the enzymes lacks sequence specificity and thus can generate Aβ of varying (39-43) lengths. The toxic forms of Aβ cause abnormal events such as apoptosis, free radical formation, aggregation and inflammation.

Presenilin encodes the protease responsible for cleaving APP into Aβ. There are two forms—PS1 and PS2. Mutations in PS1, causing production of Aβ$_{42}$, are the typical cause of early onset AD.

Cholesterol-reducing agents have been alleged to have AD-preventative capabilities, although no definitive evidence has linked elevated cholesterol to increased risk of AD. However, the discovery that Aβ contains a sphingolipid binding domain lends further credence to this theory.

Similarly, ApoE, which is involved in the redistribution of cholesterol, is now believed to contribute to AD development. Individuals having the ε4 allele, which exhibits the least degree of cholesterol efflux from neurons, are more likely to develop AD.

Tau protein, associated with microtubules in normal brain, forms paired helical filaments (PHFs) in AD-affected brains which are the primary constituent of neurofibrillary tangles. Recent evidence suggests that Aβ proteins may cause hyper-phosphorylation of Tau proteins, leading to disassociation from microtubules and aggregation into PHFs.

For AD, drugs have been used to limit the progression of the disease and to alleviate or improve certain of the associated symptoms. These drug generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal are just some of the drugs proposed as therapeutic agents for AD.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C. Huntington Disease

Huntington disease, also called Huntington's chorea, chorea major, or HD, is a genetic neurological disorder characterized by abnormal body movements called chorea and a lack of coordination; it also affects a number of mental abilities and some aspects of behavior. In 1993, the gene causing HD was found, making it one of the first inherited genetic disorders for which an accurate test could be performed. The accession number for Huntingtin is NM_002111.

The gene causing the disorder is dominant and may, therefore, be inherited from a single parent. Global incidence varies, from 3 to 7 per 100,000 people of Western European descent, down to 1 per 1,000,000 of Asian and African descent. The onset of physical symptoms in HD occur in a large range around a mean of a person's late forties to early fifties. If symptoms become noticeable before a person is the age of twenty, then their condition is known as Juvenile HD.

A trinucleotide repeat expansion occurs in the Huntingtin gene, which produces mutant Huntingtin protein. The presence of this protein increases the rate of neuron cell death in select areas of the brain, affecting certain neurological functions. The loss of neurons isn't fatal, but complications caused by symptoms reduce life expectancy. There is currently no proven cure, so symptoms are managed with a range of medications and supportive services.

Symptoms increase in severity progressively, but are not often recognised until they reach certain stages. Physical symptoms are usually the first to cause problems and be noticed, but these are accompanied by cognitive and psychiatric ones which aren't often recognized. Almost everyone with HD eventually exhibits all physical symptoms, but cognitive symptoms vary, and so any psychopathological problems caused by these, also vary per individual. The symptoms of juvenile HD differ in that they generally progress faster and are more likely to exhibit rigidity and bradykinesia instead of chorea and often include seizures.

The most characteristic symptoms are jerky, random, and uncontrollable movements called chorea, although sometimes very slow movement and stiffness (bradykinesia, dystonia) can occur instead or in later stages. These abnormal movements are initially exhibited as general lack of coordination, an unsteady gait and slurring of speech. As the disease progresses, any function that requires muscle control is affected, this causes reduced physical stability, abnormal facial expression, impaired speech comprehensibility, and difficulties chewing and swallowing. Eating difficulties commonly cause weight loss. HD has been associated with sleep cycle disturbances, including insomnia and rapid eye movement sleep alterations.

Selective cognitive abilities are progressively impaired, including executive function (planning, cognitive flexibility, abstract thinking, rule acquisition, initiating appropriate actions and inhibiting inappropriate actions), psychomotor function (slowing of thought processes to control muscles), perceptual and spatial skills of self and surrounding environment, selection of correct methods of remembering information (but not actual memory itself), short-term memory, and ability to learn new skills, depending on the pathology of the individual. Psychopathological symptoms vary more than cognitive and physical ones, and may include anxiety, depression, a reduced display of emotions (blunted affect) and decreased ability to recognize negative expressions like anger, disgust, fear or sadness in others, egocentrism, aggression, and compulsive behavior. The latter can cause, or worsen, hypersexuality and addictions such as alcoholism and gambling.

HD is autosomal dominant, needing only one affected allele from either parent to inherit the disease. Although this generally means there is a one in two chance of inheriting the disorder from an affected parent, the inheritance of HD is more complex due to potential dynamic mutations, where DNA replication does not produce an exact copy of itself. This can cause the number of repeats to change in successive generations. This can mean that a parent with a count close to the threshold, may pass on a gene with a count either side of the threshold. Repeat counts maternally inherited are usually similar, whereas paternally inherited ones tend to increase. This potential increase in repeats in successive generations is known as anticipation. In families where neither parent has HD, new mutations account for truly sporadic cases of the disease. The frequency of these de novo mutations is extremely low.

Homozygous individuals, who carry two mutated genes because both parents passed on one, are rare. While HD seemed to be the first disease for which homozygotes did not differ in clinical expression or course from typical heterozygotes, more recent analysis suggest that homozygosity affects the phenotype and the rate of disease progression though it does not alter the age of onset suggesting that the mechanisms underlying the onset and the progression are different.

Huntingtin protein is variable in its structure as there are many polymorphisms of the gene which can lead to variable numbers of glutamine residues present in the protein. In its wild-type (normal) form, it contains 6-35 glutamine residues; however, in individuals affected by HD, it contains between 36-155 glutamine residues. Huntingtin has a predicted mass of ~350 kDa, however, this varies and is largely dependent on the number of glutamine residues in the protein. Normal huntingtin is generally accepted to be 3144 amino acids in size.

Two transcriptional pathways are more extensively implicated in HD—the CBP/p300 and Sp1 pathways—and these are transcription factors whose functions are vital for the expression of many genes. The postulated relationship between CBP and HD stems from studies showing that CBP is found in polyglutamine aggregates (see Kazantsev et al., 1999). Consequently, it was demonstrated that huntingtin and CBP interact via their polyglutamine stretches, that huntingtin with an expanded polyglutamine tract interferes with CBP-activated gene expression, and that overexpression of CBP rescued polyglutamine-induced toxicity in cultured cells (Nucifora et al., 2001; Steffan et al., 2001). Mutant huntingtin was also shown to interact with the acetyltransferase domain of CBP and inhibit the acetyltransferase activity of CBP, p300, and the p300/CBP-associated factor P/CAF (Steffan et al., 2001).

These observations prompted a hypothesis whereby the pathogenic process was linked to the state of histone acetylation; specifically, mutant huntingtin induced a state of decreased histone acetylation and thus altered gene expression. Support for this hypothesis was obtained in a Drosophila HD model expressing an N-terminal fragment of huntingtin with an expanded polyglutamine tract in the eye. Administration of inhibitors of histone deacetylase arrested the neurodegeneration and lethality (Steffan et al., 2001). Protective effects of HDAC inhibitors have been reported for other polyglutamine disorders, prompting the concept that at least some of the observed effects in polyglutamine disorders are due to alterations in histone acetylation (Hughes, 2002). Studies published in 2002 revealed that the N-terminal fragment of huntingtin and intact huntingtin interact with Sp1 (Dunah et al., 2002; Li et al., 2002), a transcriptional activator that binds to upstream GC-rich elements in certain promoters. It is the glutamine-rich transactivation domain of Sp1 that selectively binds and directs core components of the general transcriptional complex such as TFIID, TBP and other TBP-associated factors to Sp1-dependent sites of transcription. In vitro transcription studies have gone on to show that in addition to targeting Sp1, mutant huntingtin targets TFIID and TFIIF, members of the core transcriptional complex (Zhai et al. 2005). Mutant huntingtin was shown to interact with the RAP30 subunit of TFIIF. Notably, overexpression of RAP30 alleviated both mutant huntingtin-induced toxicity and transcriptional repression of the dopamine D2 receptor gene. These results indicate that mutant huntingtin may interfere with multiple components of the transcription machinery.

There is no treatment to fully arrest the progression of the disease, but symptoms can be reduced or alleviated through the use of medication and care methods. Huntington mice models exposed to better husbandry techniques, especially better access to food and water, lived much longer than mice that were not well cared for.

Standard treatments to alleviate emotional symptoms include the use of antidepressants and sedatives, with antipsychotics (in low doses) for psychotic symptoms. Speech therapy helps by improving speech and swallowing methods; this therapy is more effective if started early on, as the ability to learn is reduced as the disease progresses. A two-year pilot study, of intensive speech, pyschiatric and physical therapy, applied to inpatient rehabilitation, showed motor decline was greatly reduced.

Nutrition is an important part of treatment; most third and fourth stage HD sufferers need two to three times the calories of the average person to maintain body weight. Healthier foods in pre-symptomatic and earlier stages may slow down the onset and progression of the disease. High calorie intake in pre-symptomatic and earlier stages has been shown to speed up the onset and reduce IQ level. Thickening agent can be added to drinks as swallowing becomes more difficult, as thicker fluids are easier and safer to swallow. The option of using a stomach PEG is available when eating becomes too hazardous or uncomfortable; this greatly reduces the chances of aspiration of food, and the subsequent increased risk of pneumonia, and increases the amount of nutrients and calories that can be ingested.

EPA, an Omega-3 fatty acid, may slow and possibly reverse the progression of the disease. As of April 2008, it is in FDA clinical trial as ethyl-EPA, (brand name Miraxion), for prescription use. Clinical trials utilise 2 grams per day of EPA. In the United States, it is available over the counter in lower concentrations in Omega-3 and fish oil supplements.

2. Cancer

The present invention also involves, in another embodiment, the treatment of cancer. The types of cancer that may be treated, according to the present invention, is limited only by the involvement of Cdk5/p25. Thus, it is contemplated that a wide variety of tumors may be treated, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

Tumor cell resistance to cancer therapies represents a major problem in clinical oncology. One goal of current cancer research is to find ways to improve the efficacy of chemo- and radiotherapy. One way is by combining such traditional therapies with new therapies such like those disclosed here. In the context of the present invention, it is contemplated that p25 antibody therapy could be used similarly in conjunction with chemo- or radiotherapeutic intervention.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Killin expression construct is particularly preferred as this compound.

In treating cancer according to the invention, one would contact the tumor cells with an agent in addition to the p25 antibody. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a p25 antibody, as described above.

Agents that directly cross-link nucleic acids, specifically DNA, are envisaged to facilitate DNA damage leading to a synergistic, antineoplastic combination with p25 antibody. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

3. Neuronal Insult

Yet another therapeutic application of p25 antibodies is in the realm of neuronal insults. In particular, insults caused by hypoxia, ischemia, stroke, retinal degeneration, epilepsy, cerebral palsy, myocardial infarction, or spinal chord injury can induce Cdk5/p25-mediated damage which can be blunted by the use of p25-selective antibodies.

Stroke (sometimes called a cerebrovascular accident) is the rapidly developing loss of brain function(s) due to disturbance in the blood supply to the brain, caused by a blocked or burst blood vessel. This can be due to ischemia (lack of blood flow) caused by thrombosis or arterial embolism or due to a hemorrhage. As a result, the affected area of the brain is unable to function, leading to inability to move one or more limbs on one side of the body, inability to understand or formulate speech, or inability to see one side of the visual field. Stroke is the leading cause of adult disability in the United States and Europe. It is the number two cause of death worldwide and may soon become the leading cause of death worldwide. Risk factors for stroke include advanced age, hypertension (high blood pressure), previous stroke or transient ischemic attack (TIA), diabetes, high cholesterol, cigarette smoking and atrial fibrillation. High blood pressure is the most important modifiable risk factor of stroke.

A stroke is occasionally treated with a thrombolytic in a stroke unit. Secondary prevention may involve antiplatelet drugs (aspirin and often dipyridamole), blood pressure control, statins, and in selected patients with carotid endarterectomy and anticoagulation. Treatment to recover lost function is stroke rehabilitation, involving health professions such as speech and language therapy, physiotherapy and occupational therapy.

Myocardial infarction (MI) or acute myocardial infarction (AMI), commonly known as a heart attack, is the interruption of blood supply to part of the heart, causing heart cells to die. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. The resulting ischemia (restriction in blood supply) and oxygen shortage, if left untreated for a sufficient period of time, can cause damage or death (infarction) of heart muscle tissue (myocardium).

Heart attacks are the leading cause of death for both men and women worldwide. Important risk factors are previous cardiovascular disease, older age, tobacco smoking, high blood levels of certain lipids (triglycerides, low-density lipoprotein) and low levels of high density lipoprotein (HDL), diabetes, high blood pressure, obesity, chronic kidney disease, heart failure, excessive alcohol consumption, the abuse of certain drugs (such as cocaine and methamphetamine), and chronic high stress levels.

V. EXAMPLES

The following examples are included to further illustrate various aspects of the invention and should not be construed as limiting the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and Characterization of a Monoclonal Anti-p25 Antibody

Cdk5/p25 proteins (FIG. 2A) were co-expressed in Sf9 insect cells from a Baculovirus vector (pBAC4X-1) encoding the genes for the human proteins. The Cdk5 protein (C-terminal his-tagged) contained a mutated Asp145 to Arg145 and was inactive. The proteins were absorbed to a Ni-NTA column, eluted and further purified by FPLC S-sepharose HP column chromatography. Mice received intrasplenic injections of pure Cdk5/p25 conjugated to biodegradable microparticles to optimize antigen presentation. ELISA assays were used to initially screen mice sera for antibody production using pure Cdk5/p25 followed by Western blotting of the pure Cdk5/p25 and striatal cell lysates from a p25 (p25-GFP) over-expressing mouse line (FIG. 2B). When both assays yielded positive results, a hemisplenectomy was performed and B cells were fused with SP2/0-IL6 myeloma cells to make hybridomas. Hybridoma culture supernatants were screened by ELISA, immunoblotting of pure protein (FIG. 2A), and immunohistochemical staining of HEK293T cultured cells transfected with Cdk5, p35, Cdk5/p35, p25, Cdk5/p25, or negative control (blank) eukaryotic expression plasmids (FIG. 2C). Hybridoma lines producing antibodies selective for p25 were re-derived and screens were repeated.

One hybridoma cell line, 1C4 from which supernatant exhibited highest levels of specificity for p25 or p25-GFP was used to derive ascites fluid (injection of the hybridoma cells into SCID mice), from which the antibody was affinity purified using a Protein G affinity resin.

Surprisingly, the antibody does not react with p35 at all but detects transgenic p25-GFP in lysates from GFP-p25 over-expressing mice (FIG. 2B). The antibody strongly detects p25 generated in response to focal ischemia in both brain slices and cultured neurons (FIG. 3A-B). Additionally, the anti-p25 monoclonal antibody inhibits Cdk5/p25 activity but has little or no effect on PKA activity (FIG. 4).

$V_H$ and $V_L$ components of the antibodies produced by the hybridomas were be cloned sequentially into the FabD1.3myc plasmid as described by Evan et al. (1985); Ruther et al. (1981). The Fabs were expressed, purified and assessed for antigen specificity using the antigenic myc tag for secondary-tertiary antibody detection in immunoblots. The sequences of the heavy and light chains are presented in FIG. 5.

Example 2

Function of Aberrant Cdk5 in Ischemic Injury and Stroke

Embolic MCAO.

For MCAO, a fibrin clot was inserted into the MCA via microcatheter. Successful MCAO was confirmed by monitoring cerebral blood flow using a laser Doppler probe. See Methods for details (Dinapoli et al., 2006; Overgaard et al., 1992; Zhang et al., 1997).

Slice Pharmacology and OGD.

Acutely prepared coronal slices were prepared as described (Nishi et al., 1997). For OGD, slices were switched from Kreb's buffer bubbled in 95% $O_2$/5% $CO_2$ to 100% $N_2$ and glucose was replaced by 10 mM sucrose for indicated periods (Sahin et al., 2008; Sahin et al., 2007). Slices were treated with SKF81297 (1 µM, 10 min), calpain inhibitor 3, calpeptin (20 µM, 1 h), $Ca^{2+}$-free Krebs (1 h), and Indo A or B (1 h) at indicated concentrations. See Methods.

Quantitative Immunoblotting and Histology.

Homogenates were prepared from rapidly dissected tissue or striatal slices using standard methodology (Nishi et al., 1997). Abs to p35, DARPP-32 (Nishi et al., 1997), GFAP, and p25 were used to stain rat coronal cryosections (20 µm) from control and stroked hemispheres. Fluoro-Jade B staining was conducted according to the manufacturer's instructions (Millipore). For immunostaining of cultured cells, rat primary striatal neuron cultures were prepared, subjected to control or OGD conditions, fixed and stained as described (Meyer et al., 2008). Viability staining using TTC staining was conduced as described (Yang et al., 1998). See Methods for further details.

Neurophysiology.

Electrophysiological recordings of FPs and single unit activity were taken from slices under physiological and OGD conditions using described methodology (Calabresi et al., 1998; Picconi et al., 2003; Costa et al., 2006).

Animals, Animal Care and Cdk5 CKO.

Adult, male Cdk5 CKO mice were generated as described previously (Hawasli et al., 2007). Mice and rats were maintained on a 12 h light/dark cycle with access to food and water ad libitum. All experiments were approved by The UT Southwestern and West Virginia University Animal Care and Use Committees, or by Istituto Superiore Sanità (Italy), and conducted in accordance with NIH guidelines and European Communities Council Directive of November 1986 (86/609/ECC).

p25 is a Biomarker for Brain Ischemic Stroke Injury.

Figure 7C:
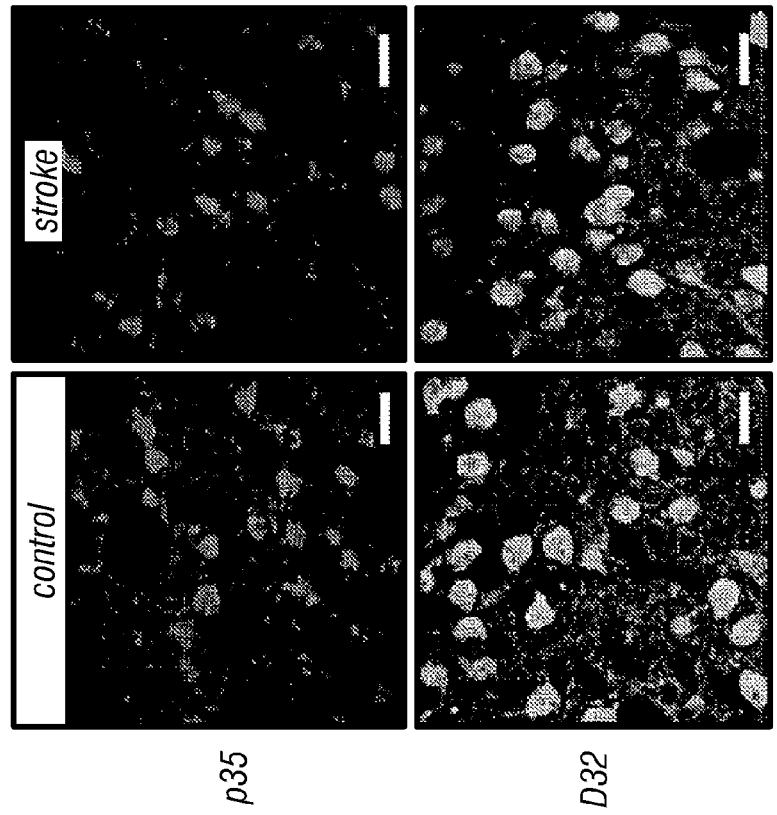
Figure 7B:
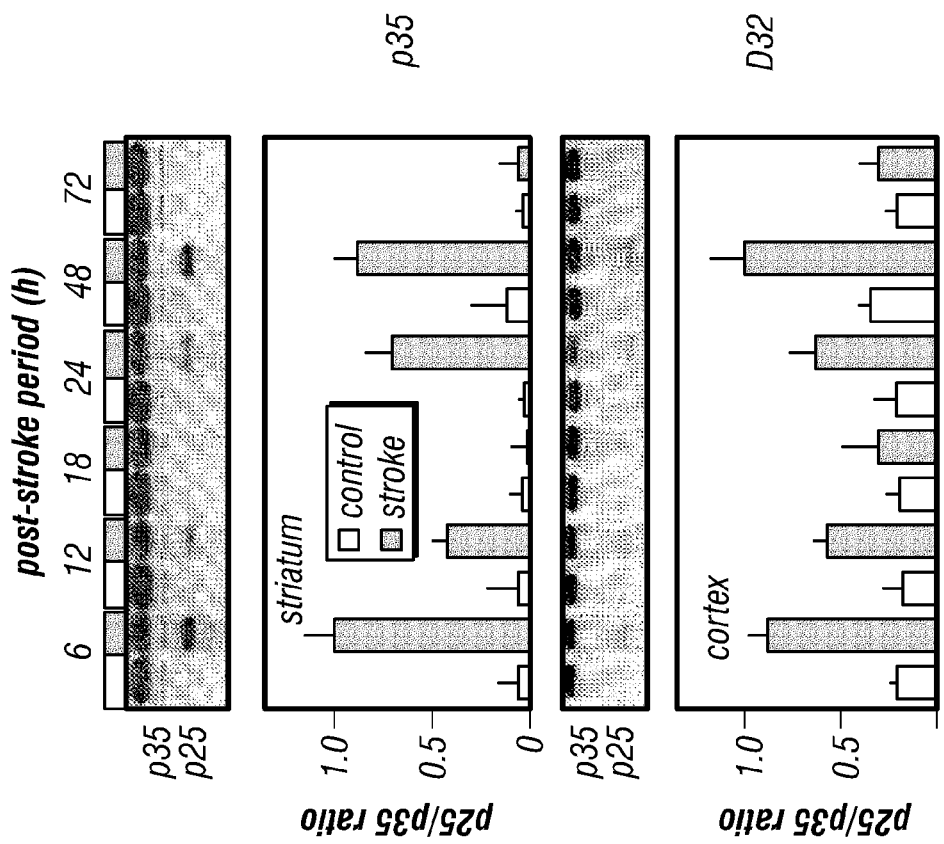

To explore the role of aberrant Cdk5/p25 in ischemic stroke, the inventors employed a clinically relevant animal model in which focal ischemia is achieved by selective unilateral embolization of the middle cerebral artery in aged rats. In this model, vascular reperfusion is established after 2 h of MCAO by the administration of tPA (Dinapoli et al., 2006). Using this paradigm, we found that ischemic stroke induced robust p25 generation in aged rat brain (FIG. 7B). Unilateral MCAO caused marked production of p25 6 h after thrombolysis in striatum. Interestingly, levels abated at 12 and 18 h before peaking again at 48 h, reflecting initial and latent phases of stroke injury. As peak levels of p25 were produced, a corresponding drop in the level of the parent protein, p35 was perceptible. A similar temporal pattern occurred in prefrontal cortex but with comparatively lower levels detected. Thus p25 is generated in response to the initial focal ischemic insult and during the delayed period of spreading damage that characterizes stroke pathophysiology.

Figure 7D:
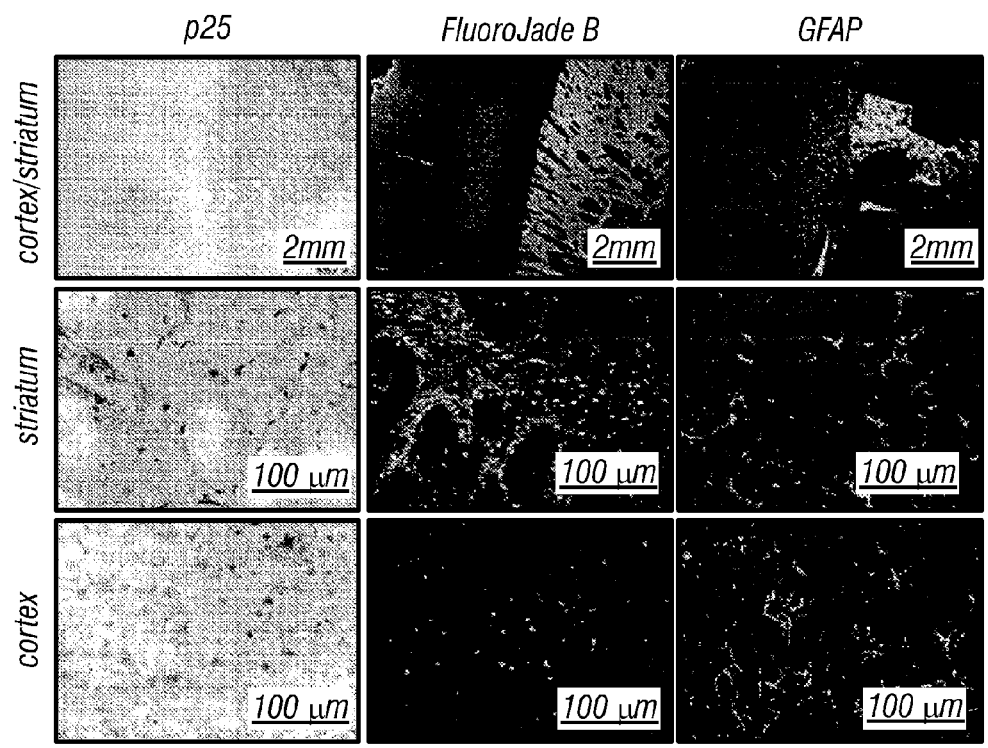
Figure 7E:
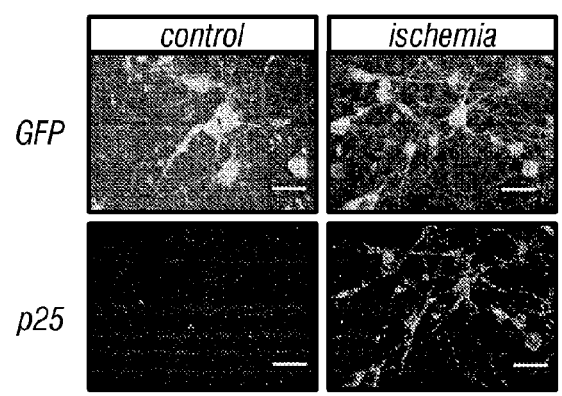

While infarcts may be detected by classic histopathology or in vivo imaging, there are few biomarkers for ischemia-damaged neurons. Immunostaining of infarcted regions with the striatal marker, DARPP-32 or p35 revealed no obvious effects on neuronal soma or neuropil architecture (FIG. 7C). Given the close relationship between ischemic insult and p25 generation, we derived a mAb that selectively detects p25. This p25 mAb only stains cells transfected with an expression vector for p25 but not p35. Furthermore, the mAb detects p25 generated by MCAO with greater sensitivity than a commercial p35/p25 Ab. This reagent detected p25 in immunostains of striatum and ipsilateral frontoparietal cortex of stroked hemispheres (FIG. 7D) p25 was found throughout the neuropil and in medium spiny neurons of the striatum and pyramidcal neurons of the cortex 6 h after reperfusion. Furthermore, p25 staining correlated with neuronal injury of these regions detected by FluorJade B. This stain binds degenerating neurons that have undergone ischemic injury and often accompanies astrogliosis and GFAP staining (Butler et al., 2002; Larsson et al., 2001). Indeed, by 24 h after reperfusion, these areas develop positive staining for the activated astocyte marker glial fibrilar acidic protein (GFPA) that accompanies ischemic injury (Clark et al., 1994; Stoll et al., 1998). To further demonstrate the generation of p25 in response to ischemic conditions, primary cultures of rat striatal neurons were subjected to oxygen and glucose deprivation (OGD) for 20 min. OGD induced p25 production throughout these cultured neurons as well (FIG. 7E). Consequently, p25 is a biomarker of ischemic injury.

Inhibition of Aberrant Cdk5 Blocks Ischemic Neuronal Death.

Figures 8C, 8D:
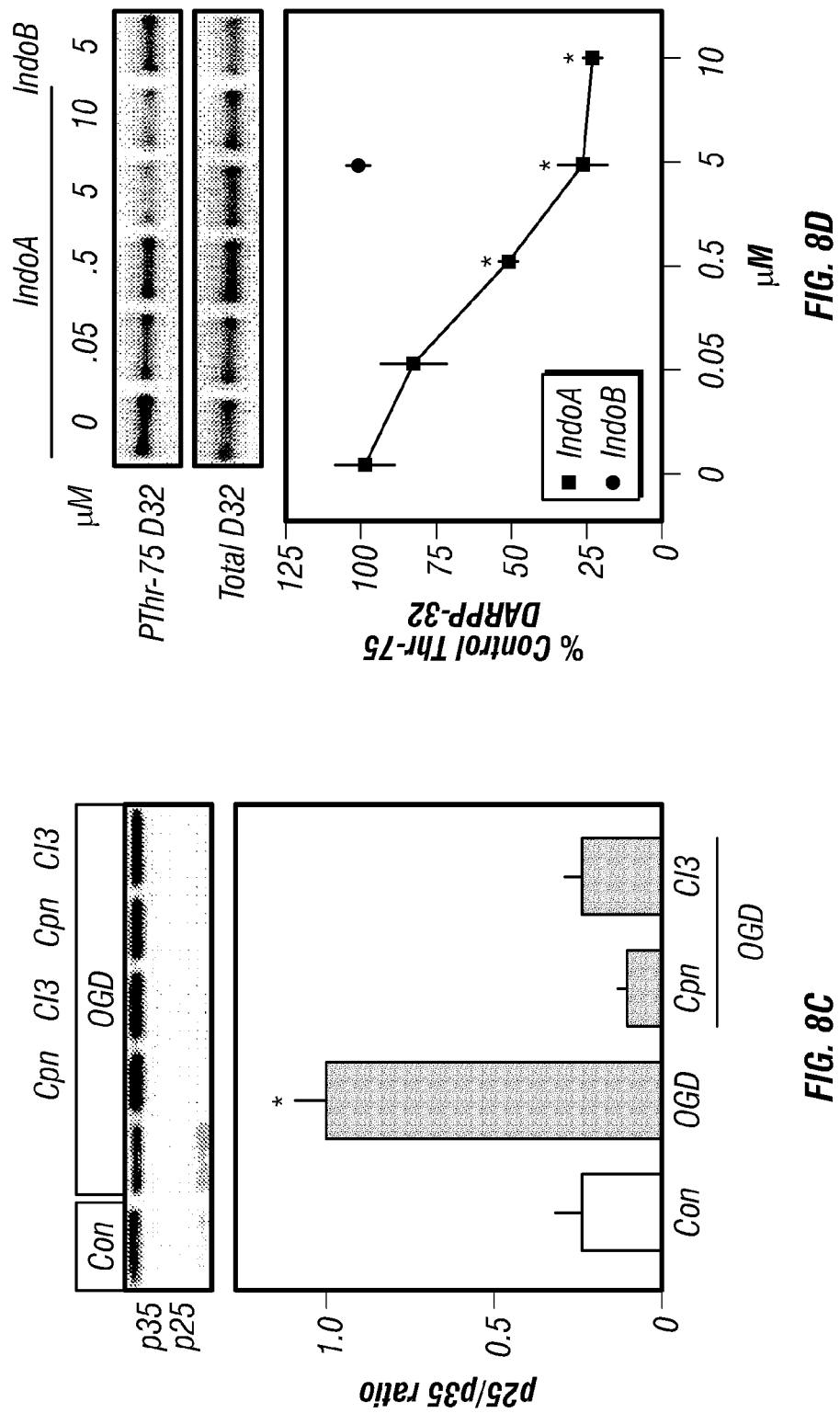

To determine the mechanisms by which ischemia caused p25 production, the lysates from acutely prepared mouse striatal slices subjected to OGD were immunoblotted for p35 and p25 (FIG. 8A). In response to OGD, p25 accumulated in a time-dependent manner. Furthermore, p25 generation was blocked by removal of $Ca^{2+}$ from the incubation buffer (FIG. 8B). Moreover, preincubation with the calpain inhibitors calpeptin or calpain inhibitor 3 prevented p25 generation (FIG. 8C). These data are consistent with the generation of p25 during ischemia as a result of cleavage of p35 via the $Ca^{2+}$-dependent activation of calpain.

To assess the deleterious effects of aberrantly active Cdk5/p25, the selective and potent Cdk5 inhibitor, indolinone A (Gillardon et al., 2005) (Indo A) was employed. First, its ability to inhibit Cdk5 in striatal slices was assessed by treating striatal slices with various concentrations (1-10 μM) of Indo A and blotting the lysates for the defined Cdk5 site, phospho-Thr75 DARPP-32 (Bibb et al., 1999). Cdk5 inhibition dose-dependently reduced phospho-Thr75, with 5 μM Indo A causing a reduction to 26±8% of basal levels. Furthermore, the $IC_{50}$ value of Indo A was defined as 0.29 μM (FIG. 8D). In contrast the congener Indolinone B, which is limited in specificity to Cdk4 (Weishaupt et al., 2003), had no effect on Cdk5-dependent phosphorylation of DARPP-32. Thus, Cdk5 is effectively inhibited in intact striatal tissue by Indo A.

Figure 8E:
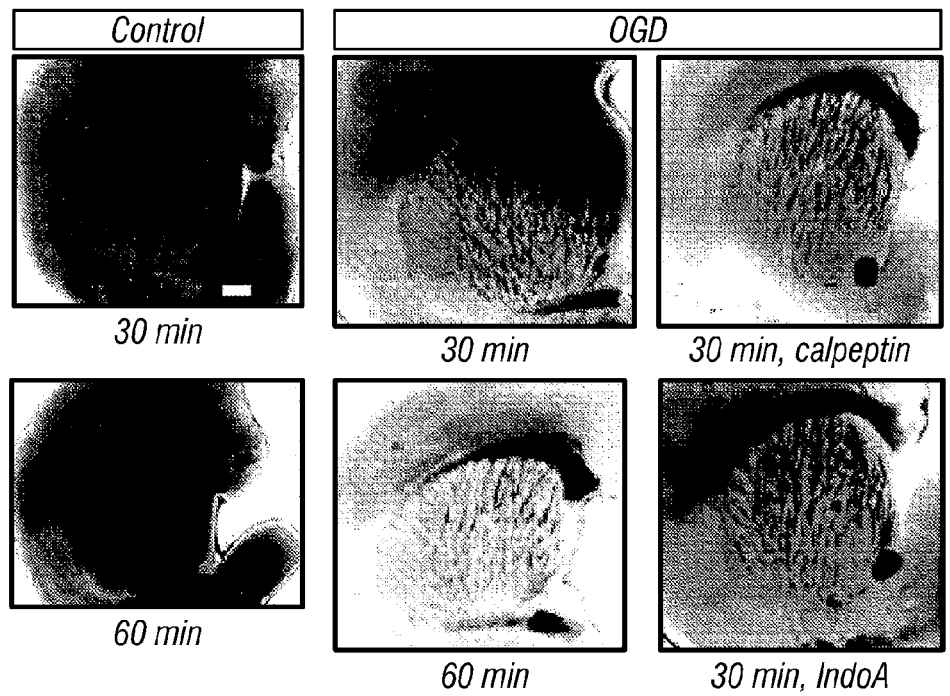
Figure 8F:
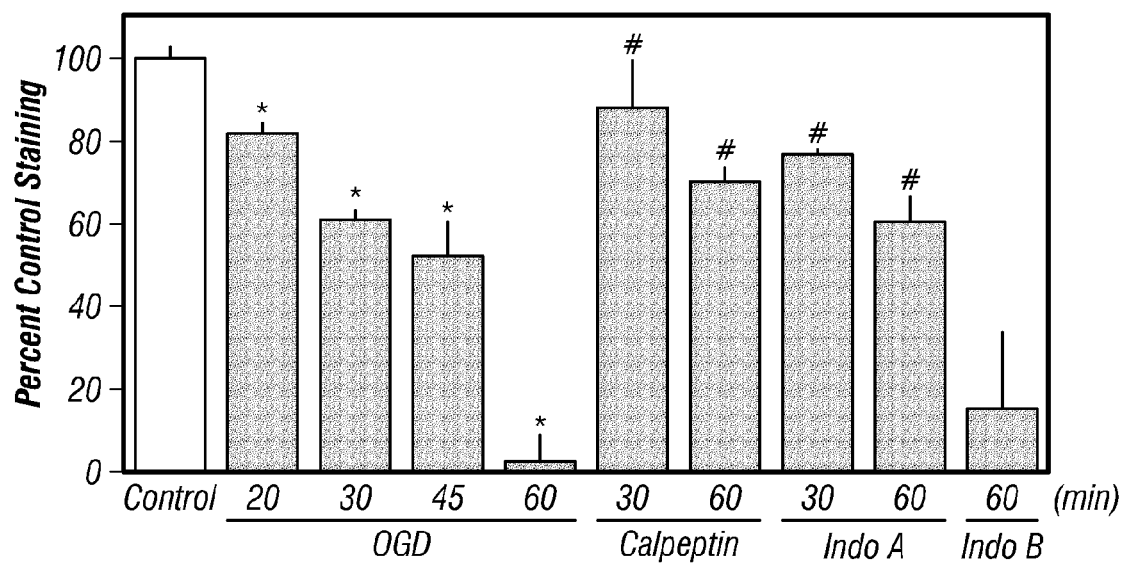

Having established this pharmacological approach, the effect of OGD on neuronal viability was next quantitatively assessed by 2, 3, 5-triphenyltetrazolium chloride (TTC) staining (Bederson et al., 1986) (FIGS. 8E and 8F). TTC staining was readily observed in coronal mouse brain slices oxygenated in Kreb's buffer for 1 h. OGD induced time-dependent neuronal death with TTC staining reduced to 60.8±2.1 and 0.6±7.9% of control levels by exposure to ischemic conditions for 30 and 60 min, respectively.

Incubation of slices with calpeptin or Indo A for 1 h prior to and during OGD significantly blocked neuronal death induced by ischemic conditions. Indeed, even after 60 min without oxygen and glucose, viability was maintained at 69.6±6.6 and 59.7±6.0% of control levels as a result of calpain or Cdk5 inhibition, respectively. Slices neuroprotected by calpeptin or Indo A stained 111.3±6.0- or 95.5±9.6-fold, respectively, more intensely than those subjected to 60 min OGD in the absence of either of these inhibitors. Indo B showed no such neuroprotective effect. These data indicate that inhibition of aberrant Cdk5 activity or calpain-cleavage of p35 during ischemia is profoundly neuroprotective.

Inhibition of Aberrant Cdk5 Protects Dopamine Neurotransmission from Ischemia.

Figure 9A:
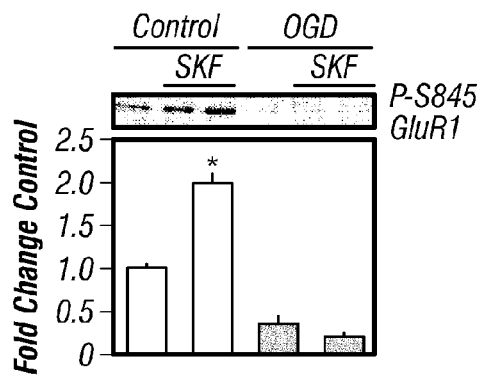
FIGS. 9A-C—Aberrant Cdk5 affects signal transduction pathways of dopaminoceptive MSNs during ischemia.
Figure 9B:
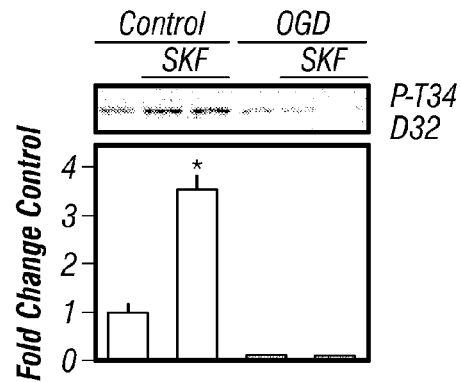

MCAO, the most frequent form of ischemic stroke in humans, prevents oxygen and nutrient delivery to large areas of the brain including the striatum. Within the striatum, dopamine neurotransmission is mediated by G protein-coupled dopamine receptors, which modulate the adenylyl cyclase/cAMP/PKA cascade (Greengard et al., 1999). To characterize the deleterious effects of ischemia on striatal neuron function, brain slices were subjected to OGD and the efficacy of the D1 dopamine receptor agonist, SKF81297 to invoke PKA-dependent phosphorylation of Thr34 of DARPP-32 or Ser845 of the GluR1 subunit of the AMPA receptor was assessed in mouse striatal slices. In oxygenated slices SKF81297 (1 μM, 5 min) induced 2.0±0.1- and 3.6±0.3-fold increases in phospho-Ser845 GluR1 and phospho-Thr34 DARPP-32, respectively (FIGS. 9A-B). However, in slices that had been subjected to OGD for 20 min, followed by 10 min of reperfusion in oxygenated buffer, this effect was completely absent and the basal level of phosphorylation of these sites was markedly attenuated.

Figure 9C:
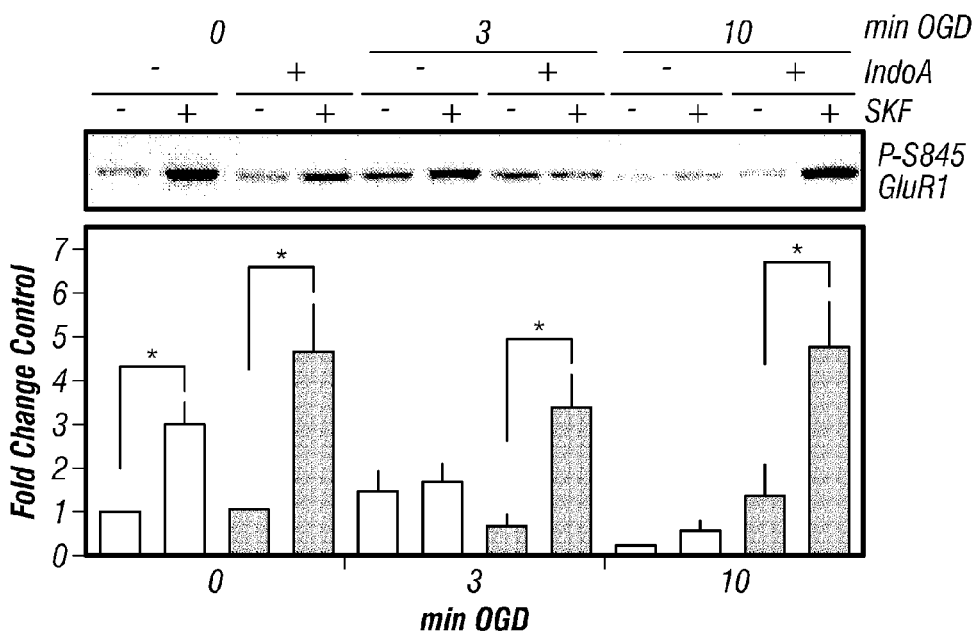

Given the severity of deleterious effects induced by 20 min of ischemia, the effects of shorter periods of OGD, including 3 and 10 min, on dopamine signaling were evaluated (FIG. 9C). While phosphorylation of Ser845 GluR1 was detectable after these shorter periods of OGD followed by re-oxygenation, even 3 min of ischemia prevented SKF81297 from inducing any increase in phospho-Ser845 GluR1. Furthermore, 10 min of OGD substantially decreased the detectable basal level of phospho-Ser845 GluR1 (18±6% of control). Interestingly, if the striatal tissue was first incubated with Indo A (10 μM, 1 h), D1 receptor-dependent signal transduction was maintained at normal levels even after 10 min of ischemia (4.7±1.2-fold increase in phospho-Ser845 in response to SKF81297). These results demonstrate the deleterious effects that even brief ischemia can have on striatal dopamine signal transduction. Furthermore, the data indicate that aberrant Cdk5 activity contributes to the loss of these signaling mechanisms in response to ischemia. Moreover, these findings demonstrate that inhibition of aberrant Cdk5 activity protects dopamine neurotransmission from ischemic injury.

Inhibition of Aberrant Cdk5 Protects Dopamine Striatal Neurons from Excitotoxic Effects and Loss of Field Potential.

Figure 10D:
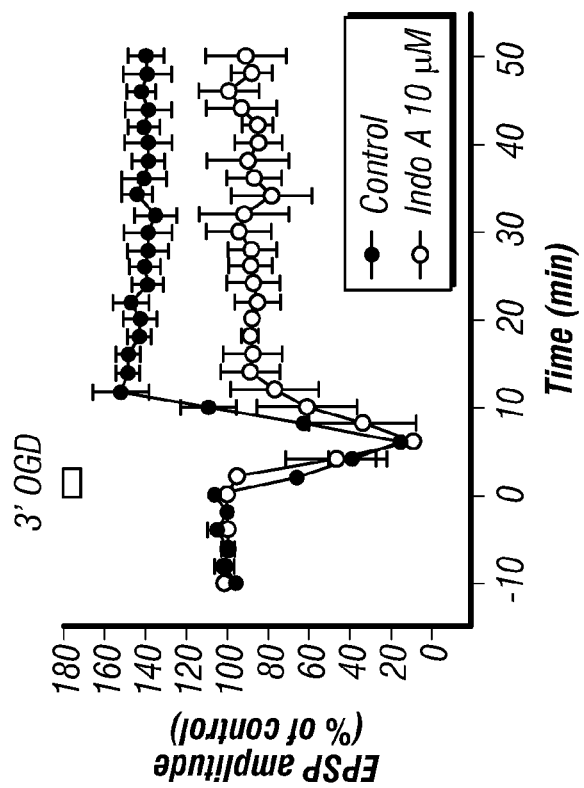
Figure 10C:
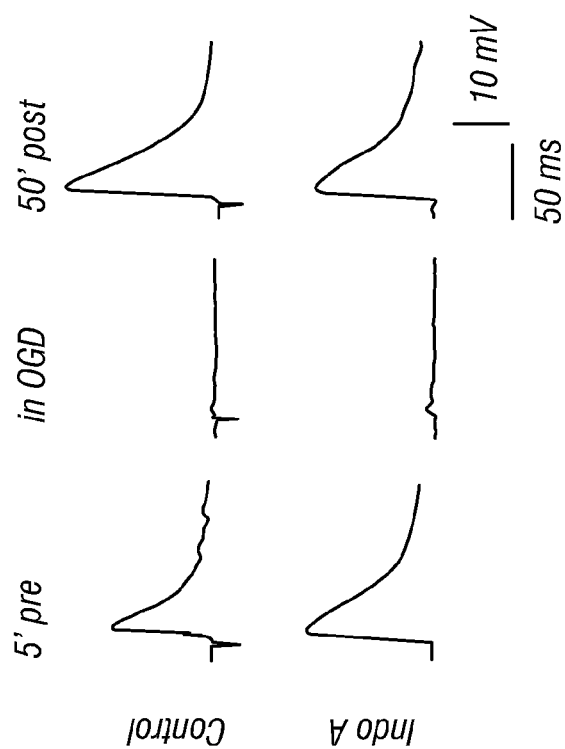
Figure 10F:
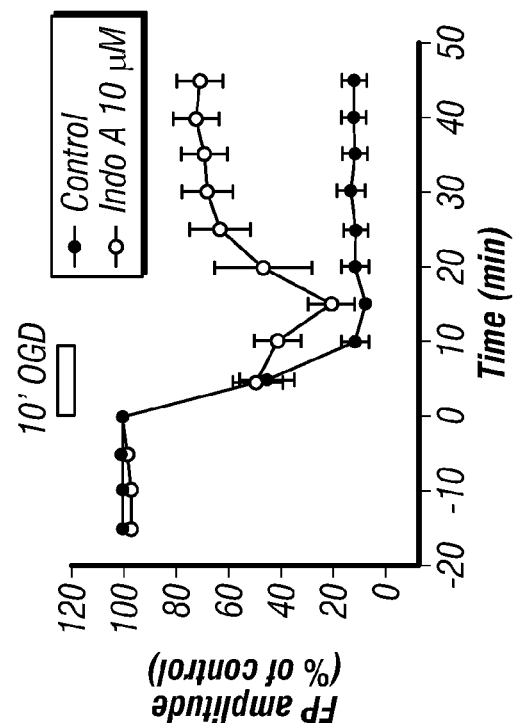
Figure 10E:
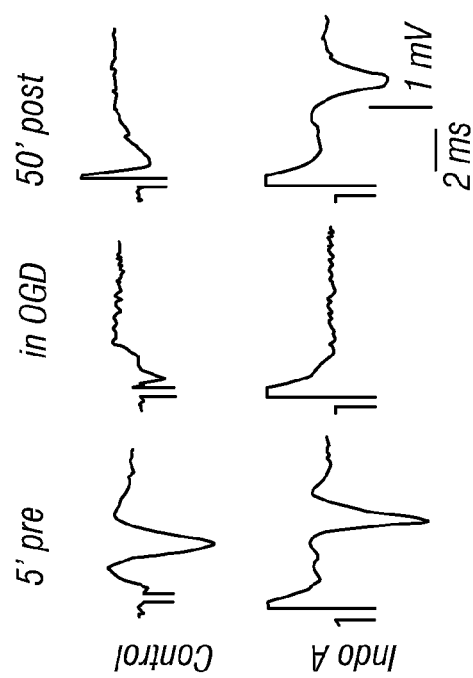

To better understand the physiological effects of shorter periods of ischemia, a neurophysiological approach was utilized. Sharp microelectrode intracellular recordings were obtained from striatal projecting spiny neurons identified according to their electrophysiological characteristics (Calabresi et al., 1998). In these neurons, a very brief period (2-3 min) of OGD induced loss of membrane potential (FIGS. 10A-B) and a transient suppression of the excitatory post-synaptic potential (EPSP) followed by a long-term increase in the EPSP amplitude in comparison to the pre-ischemic period (139.7±10.3%, n=5, p<0.05, FIG. 10C). This long-term increase of the glutamatergic transmission at corticostriatal synapses, called post-ischemic LTP (i-LTP), represents a pathological form of synaptic plasticity occurring after brain ischemia (Calabresi et al., 2003; Calabresi et al., 1998; Calabresi et al., 2002). Interestingly, pre-treatment with Indo A completely blocked the induction of i-LTP at corticostriatal synapses (n=5, p>0.05, FIGS. 10C-D) without affecting the amplitude or recovery time of the membrane depolarization induced by the brief ischemic episode (n=9, p>0.05, FIG. 10B). Extracellular field potential (FP) recordings were also obtained from corticostriatal slices. In control conditions, 10 min of OGD caused an irreversible loss of FP (FIGS. 10E-F). Conversely, the pre-treatment of corticostriatal slices with Indo A significantly reduced the loss of FP induced by ischemia. These results indicate that inhibition of aberrant Cdk5 activity neuroprotects striatum from deleterious physiological effects of ischemia associated with excitotoxicity, lose of function, and neuronal cell death.

Cdk5 CKO Protects Striatal Neurons from Ischemia-Induced Neuronal Death and Reduces Stroke Infarct Volume.

Figure 11A:
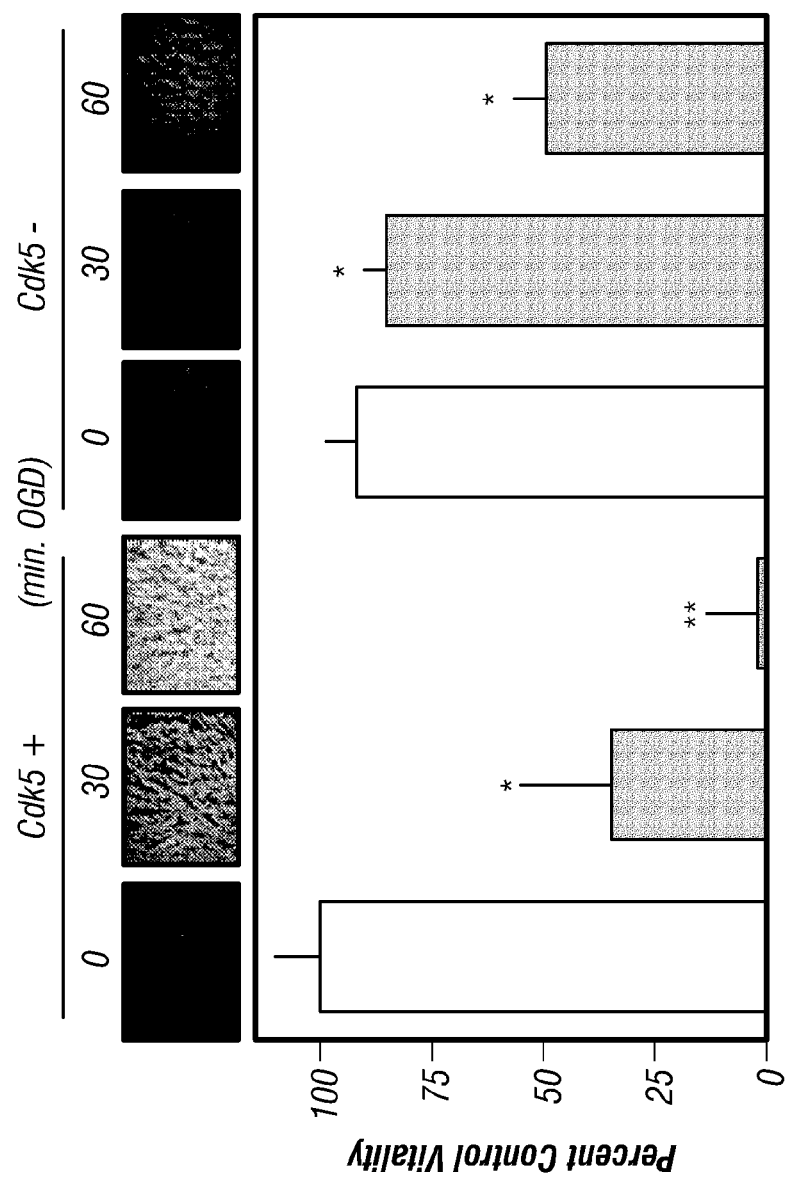

Previously we reported the generation of Cdk5 conditional knockout (CKO) mice in which a 14-day regimen of 4-hydroxytamoxifen treatment results in pan-forebrain deletion of the Cdk5 gene (Hawasli et al., 2007). Given that pharmacological inhibition of Cdk5 reduced the neurotoxic effects of OGD, the inventors hypothesized that brain slices from Cdk5 CKO mice should be neuroprotected from ischemic insult. Therefore, they compared the effects of OGD on neuronal viability of acute striatal slices from wild-type (WT) vs. CKO littermate mice (FIG. 11A). Cdk5 CKO was markedly neuroprotective. Viability in WT slices was reduced to 30±18 and 2±12% by 30 and 60 min of OGD, respectively. However Cdk5 CKO resulted in 80±4 and 49±7% viability in response to these treatments. These findings provide further evidence that aberrant Cdk5 mediates ischemic neuronal death.

To further assess the neuroprotective effects of Cdk5 CKO, MCAO was next conducted in WT vs. Cdk5 CKO mice (FIG. 11B). For these experiments groups of littermate control and Cdk5 CKO mice underwent unilateral embolic MCAO and were survived for 24 h after thrombolysis. Brains were then dissected and infarct size determined. Cdk5 CKO resulted in a profound reduction of infarct volume with striatal infarct size reduced 2.6-fold from 44.7±5.4% of total brain area for controls to 17.1%±4.4% for Cdk5 CKO mice. Furthermore, total infarct size was reduced 1.8-fold from 38.8±4.9 to 21.8±4.9% of total brain area. Surprisingly, cortical infarct volume was not significantly reduced by CKO (36.1±6.2% for controls vs. 23.8±5.3% for CKO, p=0.6, Student's t-test), suggesting that aberrant Cdk5 may contribute more meaningfully to ischemic injury in response to MCAO in striatum where highest levels of p25 are produced. These results confirm that aberrant Cdk5 is a major cause of ischemic injury and that insults caused by ischemic stroke may be greatly reduced by its inhibition.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
U.S. Pat. No. 4,816,567
WO 93/06213
Angelo et al., *J. Neurochem.*, 99:353-70, 2006.
Bederson et al., *Stroke*, 17:1304-1308, 1986.
Bibb et al., *Nature*, 402:669-671, 1999.
Bibb et al., *Nature*, 410:376-80, 2001a.
Bibb, J. A., *Neurosignals*, 12:191-199, 2003.
Brodeur et al., *Monoclonal Antibody Production Techniques and Applications*, 51-63, Marcel Dekker, Inc., NY, 1987.
Butler et al., *Brain Res. Bull.*, 929:252-260, 2002.
Calabresi et al., *Ann. Neurol.*, 43:586-597, 1998.
Calabresi et al., *Brain*, 125:844-860, 2002.
Calabresi et al., *Lancet. Neurol.*, 2:622-629, 2003.
Cheung et al., *Neuron.*, 50:13-18, 2006.

Clackson et al., *Nature*, 352, 624-628, 1991.
Clark et al., *Brain Res. Bull.*, 35:387-392, 1994.
Costa et al., *Stroke*, 37:1319-1326, 2006.
Cruz & Tsai, *Curr. Opin. Neurobiol.*, 14:390-394, 2004.
Cruz et al., *Neuron.*, 40:471-83, 2003.
David et al., *Biochemistry*, 13:1014, 1974.
De Jager et al., *Semin. Nucl. Med.*, 23(2):165-79, 1993.
Dinapoli et al., *J. Neurosci. Methods*, 154:233-238. 2006.
Doolittle and Ben-Zeev, *Methods Mol. Biol.*, 109:215-37, 1999.
Dunah et al., *Science*, 296(5576):2238-43, 2002.
Evan et al., *Mol. Cell Biol.*, 5(12), 3610-16, 1985.
Fischer et al., *Neuron.*, 48:825-38, 2005.
Gillardon et al., *Proteomics*, 5:1299-1307, 2005.
Goding, In: *Monoclonal Antibodies: Principles and Practice*, 59-104, Academic Press, 1986.
Greengard et al., *Neuron.*, 23:435-447, 1999.
Griffith et al., *EMBO J.* 12, 725-734, 1993.
Griffith, *EMBO J.* 13:3245-3260, 1994.
Gulbis and Galand, *Hum. Pathol.*, 24(12):1271-85, 1993.
Guo, *Sci. Aging Knowledge Environ.*, 50:36, 2003.
Hawasli et al., *Nat. Neurosci.*, 10:880-886, 2007.
Hughes, *Curr Biol.*, 12(4):R141-3, 2002.
Hunter et al., *Nature*, 144:945, 1962.
Jakobovits et al., *Nature*, 362, 255-258, 1993.
Jakobovits et al., *Proc. Natl. Acad. Sci. USA*, 90:2551-255, 1993.
Johnson and Chiswell, *Current Op. Structural Biol.*, 3:564-571, 1993.
Jones et al., *Nature*, 321:522-525, 1986.
Kazantsev et al., *Proc. Natl. Acad. Sci. USA*, 96(20):11404-9, 1999.
Kohler & Milstein, *Nature*, 256:495, 1975.
Kozbor, *J. Immunol.*, 133:3001, 1984.
Kusakawa et al., *J. Biol. Chem.*, 275:17116-172, 2000.
Larsson et al., *Brain Res. Bull.*, 913:117-132, 2001.
Lee et al., *Nature*, 405:360-364, 2000.
Li et al., *Mol. Cell Biol.*, 22(5):1277-87, 2002.
Marks et al., *Bio/Technol.*, 10:779-783, 1992.
Marks et al., *J. Mol. Biol.*, 222:581-597, 1991.
McCafferty et al., *Nature*, 348, 552-553, 1990.
Meyer et al., *Proc. Natl. Acad. Sci. USA*, 105(47):18561-18566, 2008. Morrison et al., *Proc. Natl. Acad. Sci. USA*, 81:6851, 1984.
Munson & Pollard, *Anal. Biochem.*, 107:220, 1980.
Nakamura et al., In: *Enzyme Immunoassays: Heterogeneous and Homogeneous Systems*, Chapter 27, 1987.
Nguyen & Bibb, *J. Cell. Biol.*, 163:697-99, 2003.
Nishi et al., *J. Neurosci.*, 17:8147-8155, 1997.
Nucifora et al., *Science*, 291(5512):2423-8, 2001.
Nygren, *J. Histochem. Cytochem.*, 30:407, 1982.
Ohshima et al., *Proc. Natl. Acad. Sci. USA*, 93:11173-78, 1996.
Overgaard et al., *J. Cereb. Blood Flow Metab.*, 12:484-490, 1992.
Pain et al., *J. Immunol. Meth.*, 40:219, 1981.
Picconi et al., *Nat. Neurosci.*, 6:501-506, 2003.
Remington's Pharmaceutical Sciences, 15$^{th}$ ed., 33:624-652, Mack Publishing Company, Easton, Pa., 1980.
Riechmann et al., *Nature*, 332:323-327, 1988.
Ruther et al., *Nucleic Acids Res.*, 9(16):4087-98, 1981.
Sahin & Bibb, *Proc. Natl. Acad. Sci. USA*, 101:112-113, 2004.
Sahin et al., *Brain Res.*, 1129:1-14, 2007.
Sahin et al., *Eur. J. Pharmacol.*, 581:270-275, 2008.
Steffan et al., *Nature*, 413(6857):739-43, 2001.
Stoll et al., *Prog. Neurobiol.*, 56:149-171, 1998.
Suresh et al., *Methods Enzymol.*, 121:210, 1986.
Verhoeyen et al., *Science*, 239:1534-1536, 1988.
Waterhouse et al., *Nucl. Acids Res.*, 21:2265-2266, 1993.
Weishaupt et al., *Mol. Cell Neurosci.*, 24:489-502, 2003.
Yang et al. *J. Neurosci. Methods*, 84:9-16, 1998.
Zhai et al., *Cell*, 123(7):1241-53, 2005.
Zhang et al., *Brain Res.*, 766:83-92, 1997.
Zola, Monoclonal Antibodies: *A Manual of Techniques*, 147-158, CRC Press, Inc., 1987.

The invention claimed is:

1. A monoclonal antibody or fragment thereof that binds to p25 but does not bind to p35, wherein said antibody or fragment thereof comprises a heavy chain variable region amino acid sequence that is the same as that encoded by SEQ ID NO: 1, and comprises a light chain variable region amino acid sequence that is the same as that encoded by SEQ ID NO: 2.

2. The antibody or fragment of claim 1, produced by the hybridoma cell line 1C4 deposited with the ATCC as PTA-8555.

3. The antibody or fragment of claim 1, wherein said antibody or fragment is a recombinant antibody or fragment.

4. The antibody or fragment thereof according to claim 1, is a humanized antibody.

5. A hybridoma that expresses an antibody that binds to p25 but does not bind to p35, wherein said antibody or fragment thereof comprises a heavy chain variable region amino acid sequence that is the same as that encoded by SEQ ID NO: 1, and comprises a light chain variable region amino acid sequence that is the same as that encoded by SEQ ID NO: 2.

6. The hybridoma of claim 5, wherein said hybridoma cell line is 1C4 and deposited with the ATCC as PTA-8555.

* * * * *

SEQUENCE LISTING

<160> NUMBER OF SEQ ID NOS: 3

<210> SEQ ID NO 1
<211> LENGTH: 354
<212> TYPE: DNA
<213> ORGANISM: Artificial Sequence
<220> FEATURE:
<223> OTHER INFORMATION: Synthetic primer

<400> SEQUENCE: 1

```
cagatccagt tggaggagtc tggacctgag ttgaggaagc ctggagagac agtcaggatc     60
tcctgcaagg cctctgggta taccttcaca actgctggaa tgcagtgggt gcaaaagatg    120
ccaggaacgg gtctgaagtg gattggctgg ataaacaccc actctggagt gccgaaatat    180
gcaggagagt tcacgggacg gtttgacttc tctttggaga cctctgccag tacggcatat    240
ttacagatag tcaacctcaa aaatgaggac acggctacgt atttctgtgc gaggtatggt    300
aagttcggcg aaatggacta ctggggtcaa ggaacctcag tcaccgtctc ctca          354
```

<210> SEQ ID NO 2
<211> LENGTH: 330
<212> TYPE: DNA
<213> ORGANISM: Artificial Sequence
<220> FEATURE:

<223> OTHER INFORMATION: Synthetic primer

<400> SEQUENCE: 2

```
attgtgatga cacaatctcc agcttctttg gctgtgtctc tggggcagag ggccaccatc    60
tcctgcagat ccagtgaaac tgttgatagt gatggcaata gttttatgca ctggtaccag   120
cagaaaccag gacagtcacc caaactcctc ttgtatcttg catccaccct agaatctggg   180
gtccctgcca ggttcagtgg cagtgggtct aggacagact tcaccctcac cattgatcct   240
gtggaggctg atgatgctgc aacctattac tgtcaccaaa ataatgagga tccgacgttc   300
ggtggaggca ccaagctgga aatcaaacgt                                    330
```

<210> SEQ ID NO 3
<211> LENGTH: 307
<212> TYPE: PRT
<213> ORGANISM: Artificial Sequence
<220> FEATURE:
<223> OTHER INFORMATION: Synthetic peptide

<400> SEQUENCE: 3

```
Met Gly Thr Val Leu Ser Leu Ser Pro Ser Tyr Arg Lys Ala Thr Leu
1               5                   10                  15

Phe Glu Asp Gly Ala Ala Thr Val Gly His Tyr Thr Ala Val Gln Asn
            20                  25                  30

Ser Lys Asn Ala Lys Asp Lys Asn Leu Lys Arg His Ser Ile Ile Ser
        35                  40                  45

Val Leu Pro Trp Lys Arg Ile Val Ala Val Ser Ala Lys Lys Lys Asn
    50                  55                  60

Ser Lys Lys Ala Gln Pro Asn Ser Ser Tyr Gln Ser Asn Ile Ala His
65                  70                  75                  80

Leu Asn Asn Glu Asn Leu Lys Lys Ser Leu Ser Cys Ala Asn Leu Ser
                85                  90                  95

Thr Phe Ala Gln Pro Pro Ala Gln Pro Ala Pro Pro Ala Ser
            100                 105                 110

Gln Leu Ser Gly Ser Gln Thr Gly Val Ser Ser Val Lys Lys Ala
            115                 120                 125

Pro His Pro Ala Ile Thr Ser Ala Gly Thr Pro Lys Arg Val Ile Val
            130                 135                 140

Gln Ala Ser Thr Ser Glu Leu Leu Arg Cys Leu Gly Glu Phe Leu Cys
145                 150                 155                 160

Arg Arg Cys Tyr Arg Leu Lys His Leu Ser Pro Thr Asp Pro Val Leu
                165                 170                 175

Trp Leu Arg Ser Val Asp Arg Ser Leu Leu Leu Gln Gly Trp Gln Asp
            180                 185                 190

Gln Gly Phe Ile Thr Pro Ala Asn Val Val Phe Leu Tyr Met Leu Cys
        195                 200                 205

Arg Asp Val Ile Ser Ser Glu Val Gly Ser Asp His Glu Leu Gln Ala
    210                 215                 220

Val Leu Leu Thr Cys Leu Tyr Leu Ser Tyr Ser Tyr Met Gly Asn Glu
225                 230                 235                 240

Ile Ser Tyr Pro Leu Lys Pro Phe Leu Val Glu Ser Cys Lys Glu Ala
                245                 250                 255

Phe Trp Asp Arg Cys Leu Ser Val Ile Asn Leu Met Ser Ser Lys Met
            260                 265                 270

Leu Gln Ile Asn Ala Asp Pro His Tyr Phe Thr Gln Val Phe Ser Asp
        275                 280                 285
```

```
Leu Lys Asn Glu Ser Gly Gln Glu Asp Lys Lys Arg Leu Leu Leu Gly
    290             295             300

Leu Asp Arg
305
```